United States Patent
Mir et al.

(10) Patent No.: US 11,931,537 B2
(45) Date of Patent: Mar. 19, 2024

(54) PRACTICE-LOADABLE MINIMALLY INVASIVE ALLERGY TEST SYSTEM

(71) Applicant: SensiVida Medical Technologies Inc., Rochester, NY (US)

(72) Inventors: Jose M. Mir, Rochester, NY (US); John P. Spoonhower, The Villages, FL (US)

(73) Assignee: SensiVida Medical Technologies INC., Rochester, NY (US)

( * ) Notice: Subject to any disclaimer, the term of this patent is extended or adjusted under 35 U.S.C. 154(b) by 583 days.

(21) Appl. No.: 17/063,267

(22) Filed: Oct. 5, 2020

(65) Prior Publication Data

US 2022/0105328 A1    Apr. 7, 2022

(51) Int. Cl.
*A61M 37/00* (2006.01)

(52) U.S. Cl.
CPC ... *A61M 37/0015* (2013.01); *A61M 2037/003* (2013.01); *A61M 2037/0053* (2013.01); *A61M 2037/0061* (2013.01); *A61M 2202/064* (2013.01); *A61M 2205/3389* (2013.01); *A61M 2205/6072* (2013.01)

(58) Field of Classification Search
CPC ........ A61M 37/0015; A61M 2037/003; A61M 2037/0053; A61M 2037/0061; A61M 2202/064; A61M 2205/3389; A61M 2205/6072; A61M 2037/0046; A61B 5/411; A61B 5/685
See application file for complete search history.

(56) References Cited

U.S. PATENT DOCUMENTS

| | | | |
|---|---|---|---|
| 5,097,810 A | 3/1992 | Fishman et al. | |
| 7,942,827 B2 | 5/2011 | Mir et al. | |
| 8,108,023 B2 | 12/2012 | Mir et al. | |
| 8,328,720 B2 | 12/2012 | Mir et al. | |
| 10,244,981 B2 | 4/2019 | Mir et al. | |
| 2007/0078414 A1* | 4/2007 | McAllister | A61B 17/205 604/232 |
| 2008/0214952 A1 | 9/2008 | Mir et al. | |
| 2008/0269635 A1 | 10/2008 | Mir et al. | |
| 2010/0030100 A1 | 2/2010 | Tokumoto et al. | |

(Continued)

*Primary Examiner* — Amber R Stiles
(74) *Attorney, Agent, or Firm* — Culhane Meadows PLLC; Robert C. Klinger

(57) ABSTRACT

An allergen-loadable microneedle cartridge is disclosed. The cartridge includes at least one substrate, a plurality of microneedles in a microneedle layout protruding from at least one substrate, and fillable allergen sites corresponding to the microneedle layout. The fillable allergen sites and microneedle layout are configured such that the microneedles can penetrate subject skin and deliver pharmacologically active doses of allergens in a minimally invasive process. A planar allergen filling system for loading the allergen-loadable microneedle cartridges is also disclosed. The system has a loading section with spaced-apart allergen loading sites that correspond to the microneedle layout of the microneedle cartridge. Filling wells having allergen deposition areas larger than the allergen loading sites transfer deposited allergen to the allergen loading sites through capillary channels. The allergen-loadable microneedle cartridge is loaded by contacting its fillable allergen sites with the loading section of the planar allergen filling device.

11 Claims, 35 Drawing Sheets

(56) References Cited

U.S. PATENT DOCUMENTS

| | | | | |
|---|---|---|---|---|
| 2010/0100005 A1* | 4/2010 | Mir | ........................ | A61B 5/411 |
| | | | | 600/556 |
| 2011/0224515 A1 | 9/2011 | Mir et al. | | |
| 2011/0270122 A1 | 11/2011 | Mir et al. | | |
| 2011/0319742 A1 | 12/2011 | Mir et al. | | |
| 2020/0368452 A1* | 11/2020 | Yang | ................... | B81C 1/00111 |

* cited by examiner

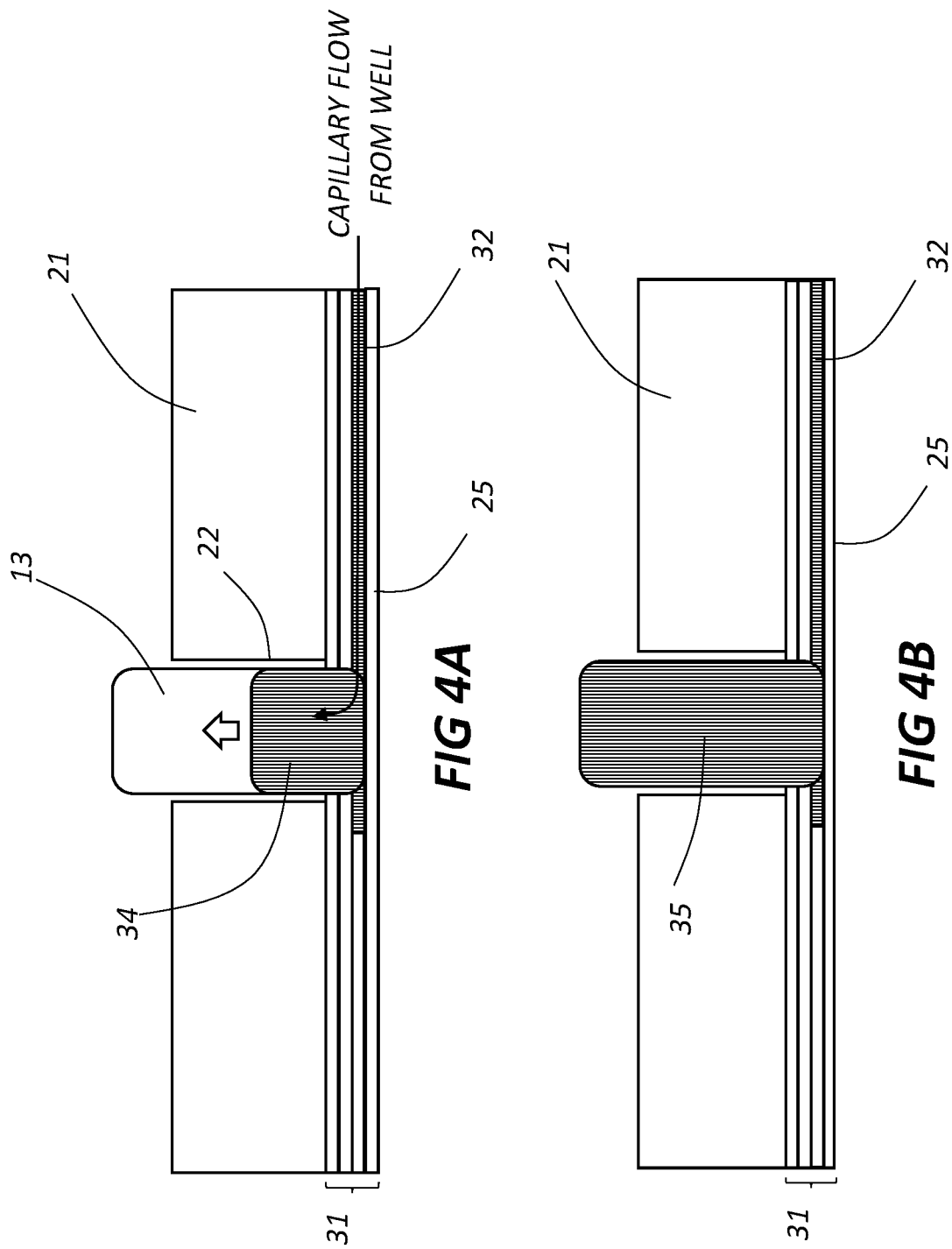

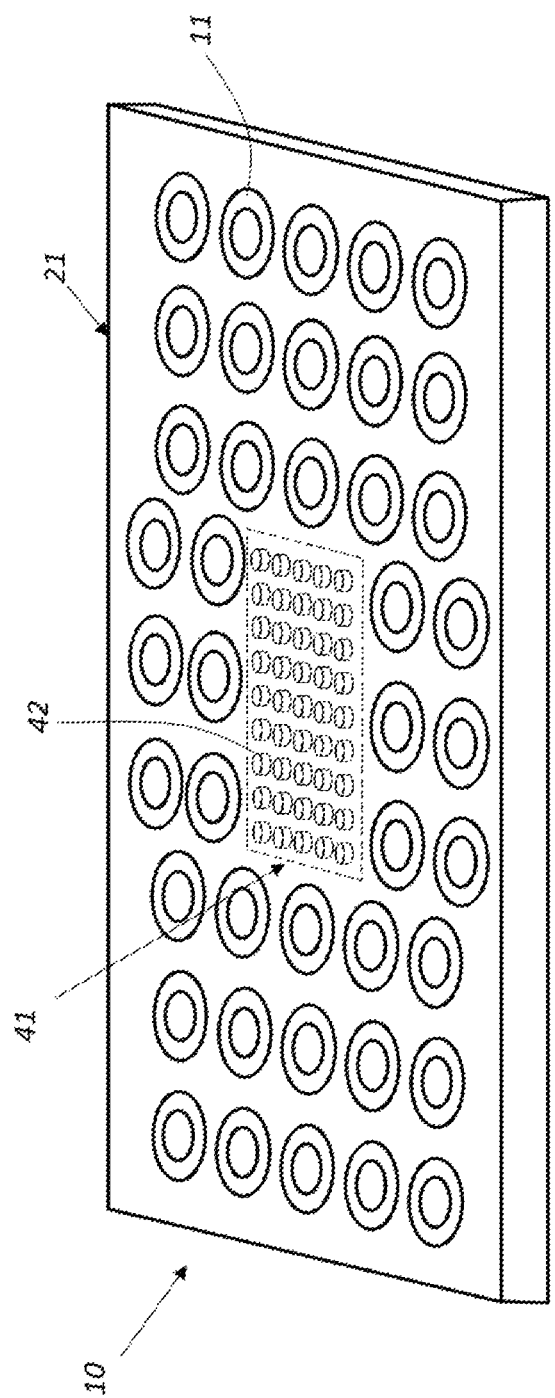

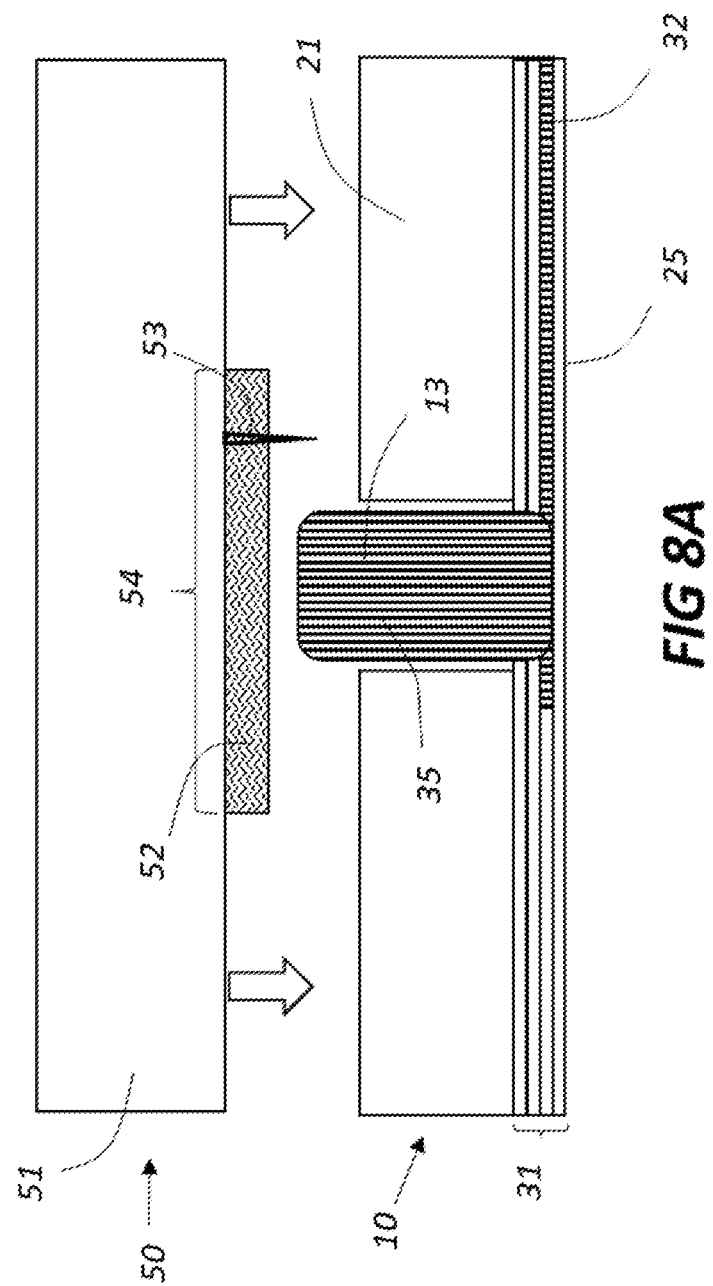

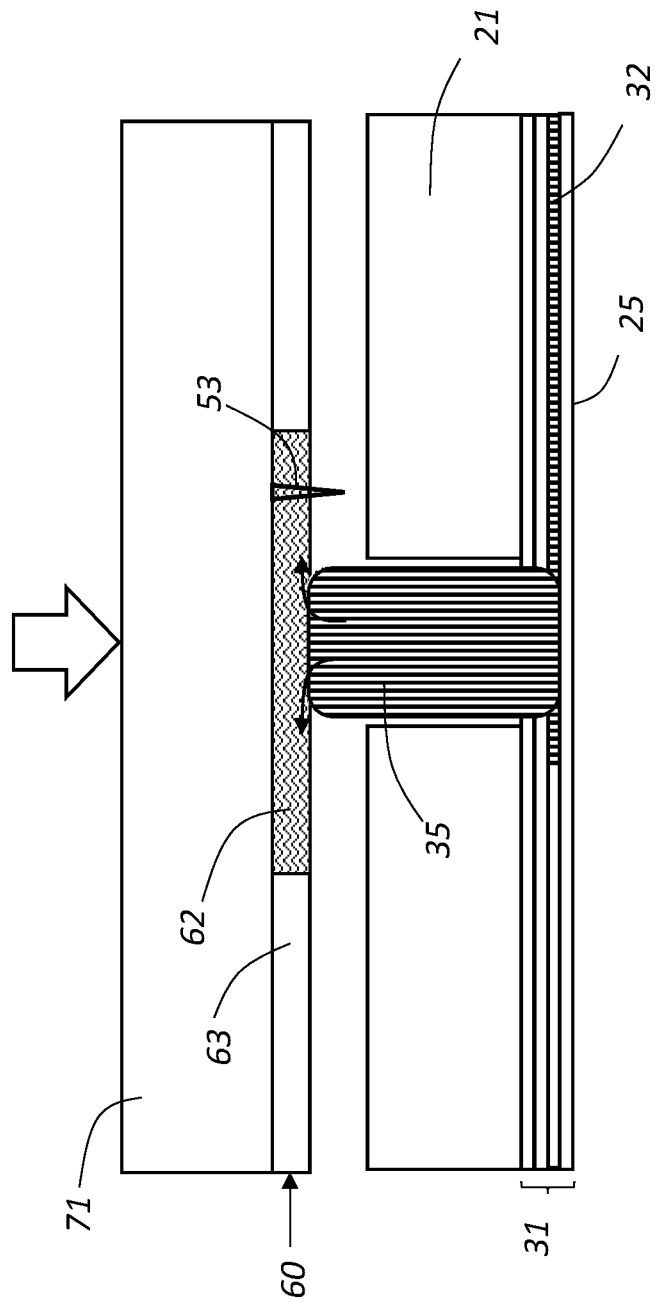

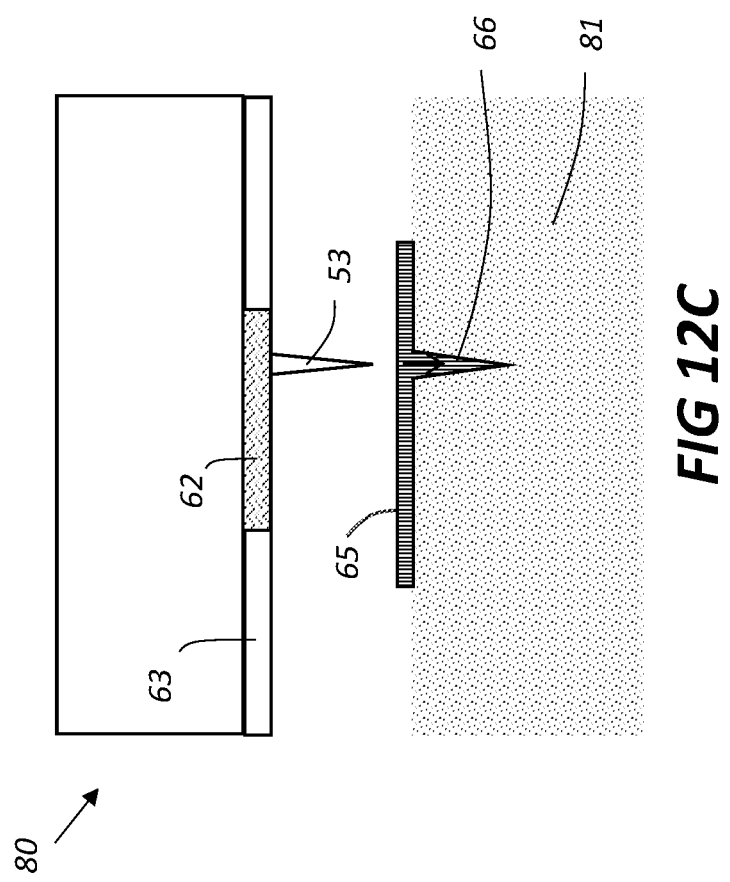

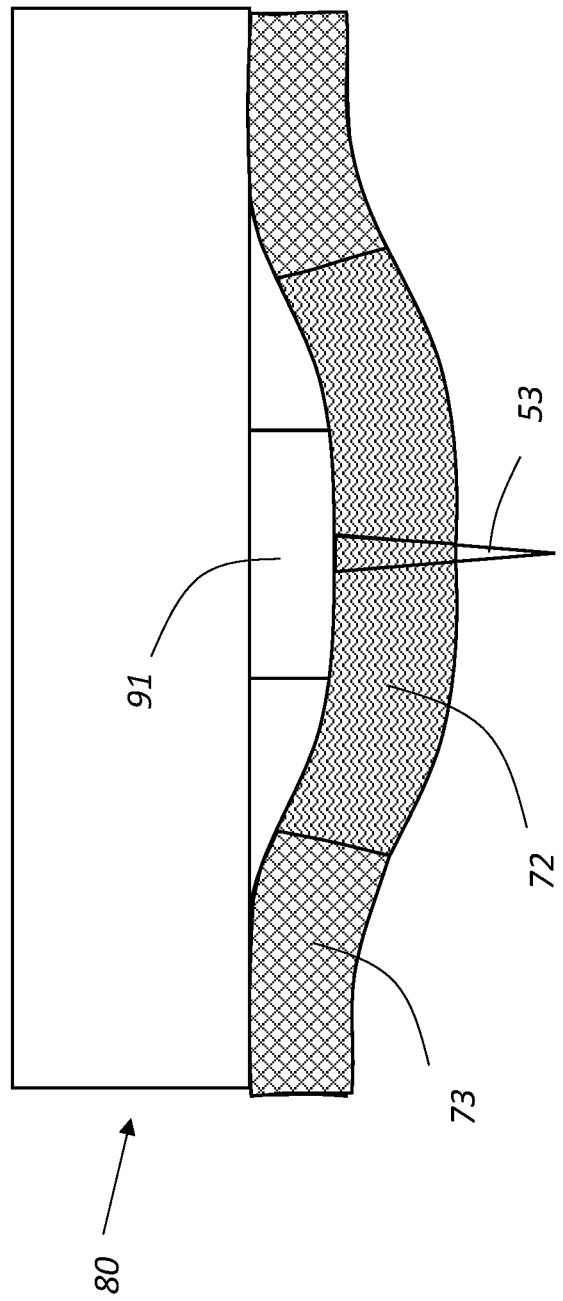

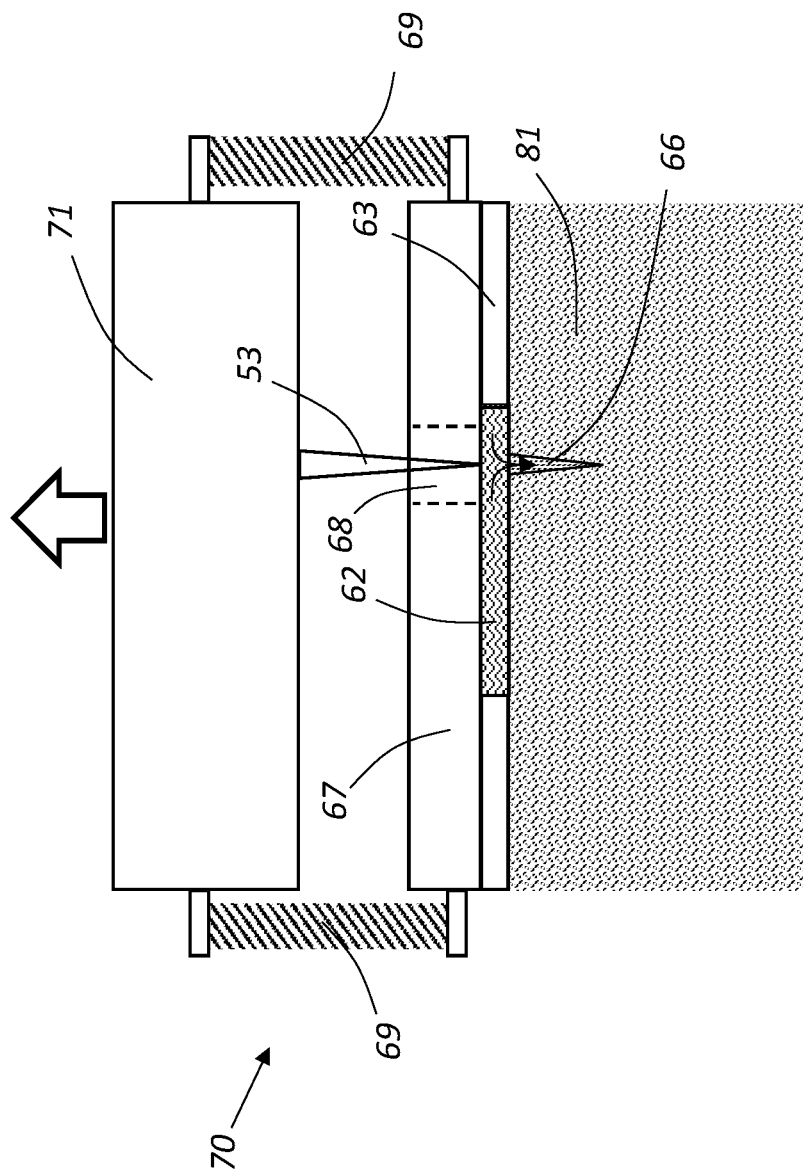

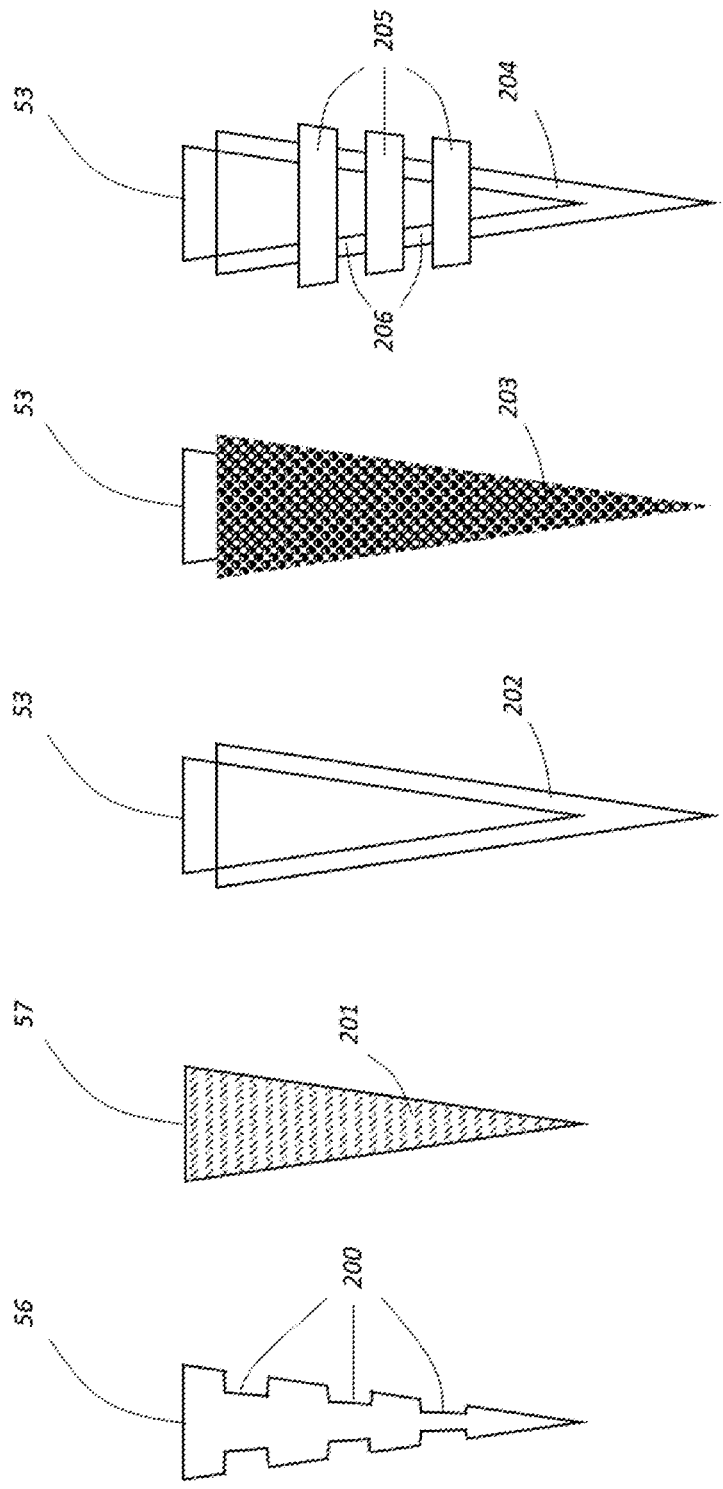

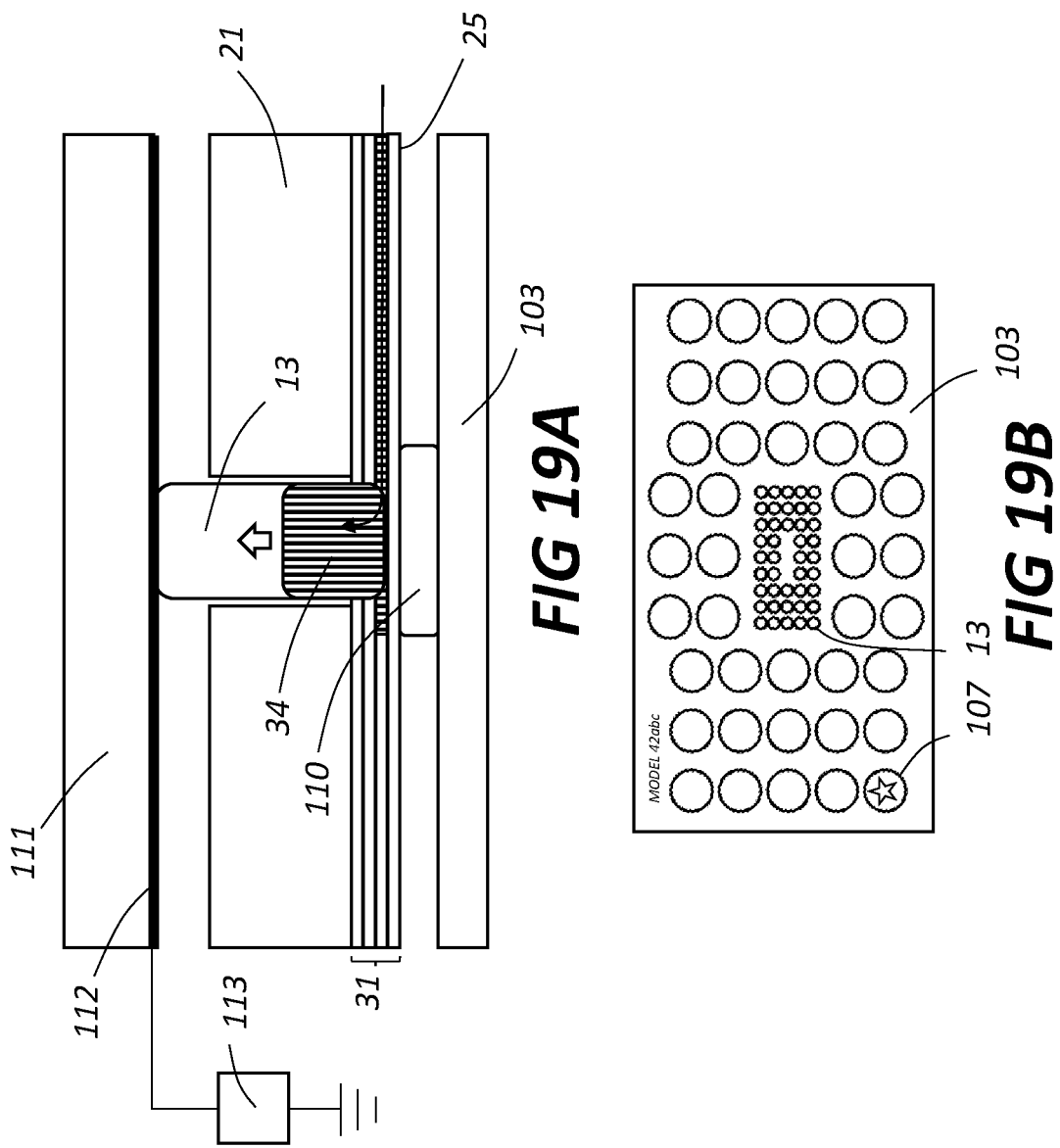

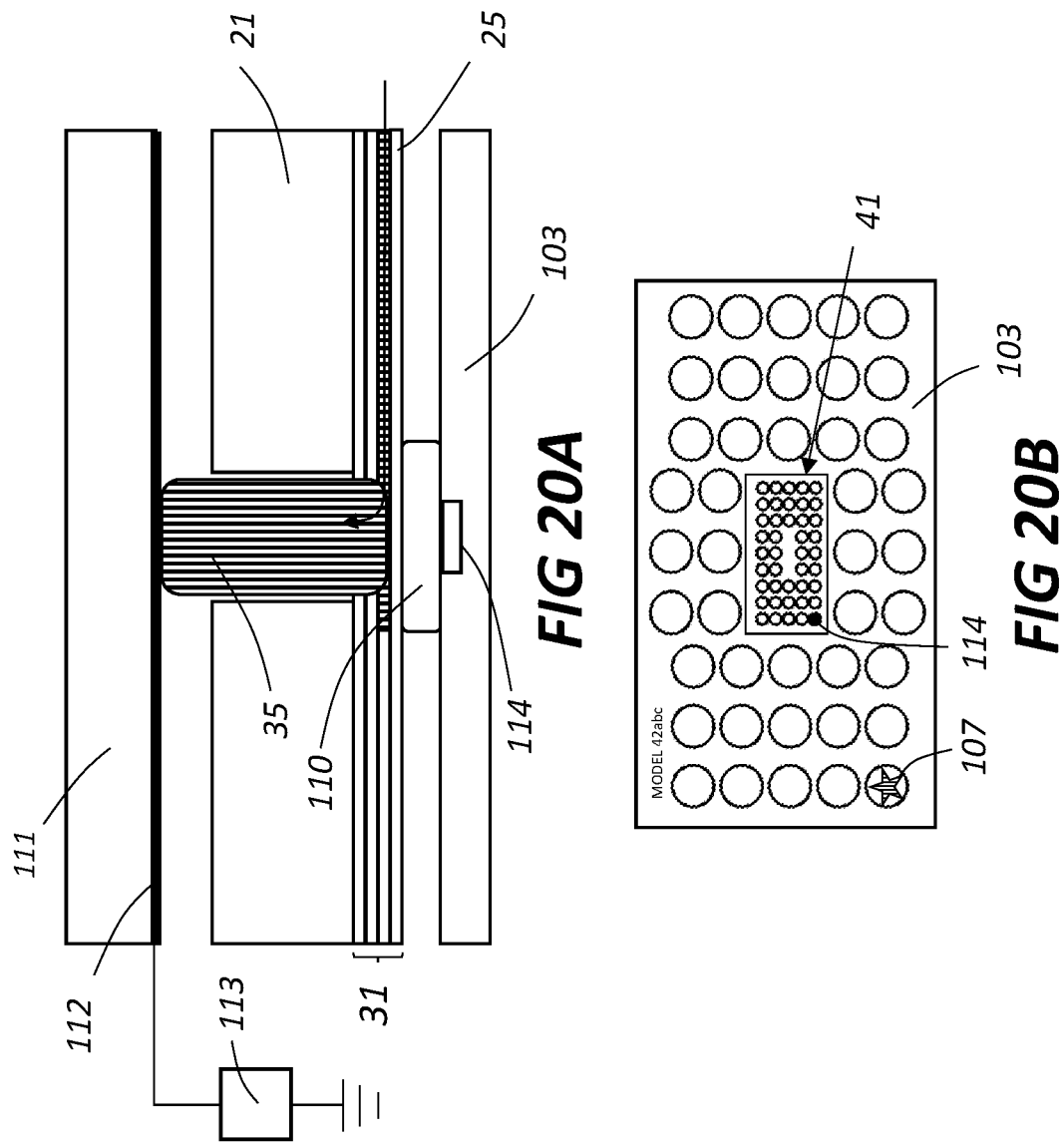

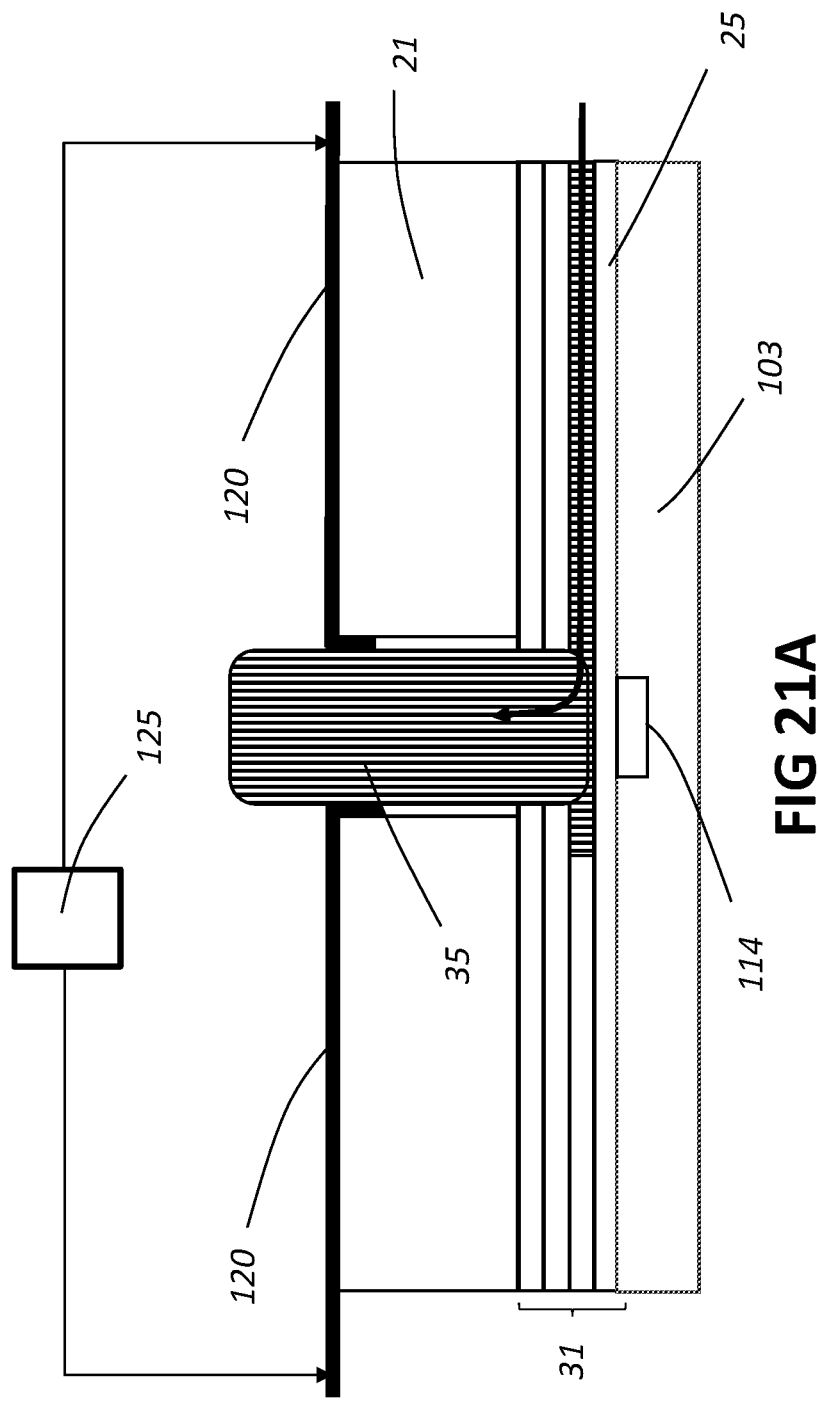

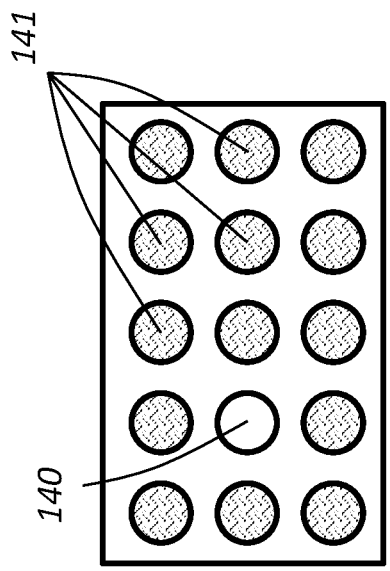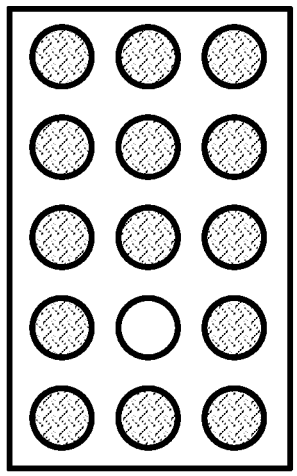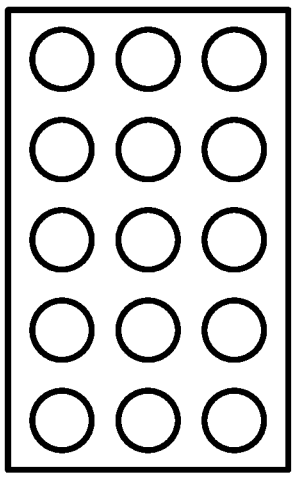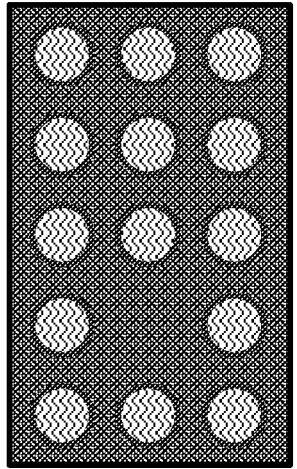
FIG 22A
FIG 22B

PRACTICE-LOADABLE MINIMALLY INVASIVE ALLERGY TEST SYSTEM

TECHNICAL FIELD

The claimed invention generally relates to devices, systems, and methods for testing medical conditions and, more particularly, to determine a degree of reaction to one or more allergens typically chosen at the medical practice for a subject, administered in a minimally invasive manner.

BACKGROUND

It is estimated that at least 50% of the U.S. population has some form of allergy. Allergy test methods such as the skin prick test are invasive and manual. They typically involve labeling the region for identification, depositing drops of allergens on the subject's skin, pricking the subject with needles, allowing 15-20 minutes for the reactions to grow before they are manually measured, and documented. Test sites are typically spaced 20-25 mm from each other to avoid possible overlap between reactions. Allergy practices typically choose "panels" of 25-30 allergens to which they often add 10-20 other allergens depending on patient symptoms, location, seasonal effects, and more.

Given the above, there is a need for a more automated, objective, less invasive allergy test that can be performed on small areas of the patient's skin using customizable allergen panels in accordance with practice and patient requirements.

SUMMARY

Novel minimally invasive allergy test devices, systems and methods are disclosed that allow reliable, simple, fast, customized filling of tightly spaced allergy test sites on a compact allergy test cartridge. The minimally invasive allergy test system includes a planar allergen filling device, an allergy test cartridge having a plurality of microneedles with associated closely spaced fillable allergen sites and may include an activation device that deploys and presses the allergy test cartridge onto the subject's skin. The microneedles and associated fillable allergen sites define a plurality of allergy test sites that can be spaced one to fifteen millimeters apart. In spite of the tight spacings, the system disclosed allows reliable manual filling of allergy test sites using standard eyedroppers or pipettes under digital control to minimize possibility of placement error.

The planar allergen filling device includes spaced-apart fillable wells that allow chosen allergens to be easily deposited. As wells are filled (to the extent desired), they provide fluidic input to thin capillary channels which transport deposited allergens at each well to corresponding "wicking posts". Wicking post distances and locations are chosen to match the cartridge's fillable allergen sites. Once allergens reach their respective wicking posts, they migrate via capillary action toward and/or to their tips for transfer to the fillable allergen sites on the allergy test cartridge. Since the amount of allergen required for each allergen test site is small, wicking posts can fill corresponding fillable allergen sites on multiple cartridges after the fillable wells are filled.

A device for guiding the deposition of allergens on specific wells of the planar filling device is disclosed. The planar filling device can be used in concert with a digital display driven by a compact computing device, e.g. a tablet, to provide guidance for filling each allergy test site. Patient ID, allergen panel, positional information of allergens on the cartridge, date, and other relevant metadata can also be displayed on the display. The digital display or projection system essentially provides the user a Graphical User Interface that identifies where drops of each allergen should be deposited. The planar filling device, if transparent or partially transparent, may be placed directly on the digital display along with positional markers, allergen ID/barcode information, and other relevant information for the test being performed. If the planar filling device is not transparent, a projection system may be used that projects information cited above on the planar filling device during the filling process. A method to obtain feedback regarding the effectiveness of allergen filling the wicking posts is disclosed using a touchscreen-based compact computing device.

An embodiment for transferring specific allergens from wicking posts to corresponding allergy test sites is disclosed. Once allergens chosen for the cartridge are deposited into wells, thin capillary channels transport the deposited allergens to corresponding wicking posts. After wicking posts are filled (to the extent desired), cartridges with allergy test sample sites are appropriately aligned and made to contact the wicking posts. A slight pressure is applied on the wicking posts to allow allergen transfer to respective fillable allergen sites. Filling is completed when fillable allergen sites are saturated (to the extent desired) with allergen, while lateral migration of allergen is hindered by surrounding hydrophobic "moats".

The claimed invention provides devices and methods for a minimally invasive allergy test system with cartridges that can be custom loaded at allergy practices. The disclosed planar allergen filling device can also be filled virtually using a Graphical User Interface that guides location and sequence of allergen loading in the filler tray.

BRIEF DESCRIPTION OF THE DRAWINGS

It will be appreciated that for purposes of clarity and where deemed appropriate, various elements in the drawings have not necessarily been drawn to scale in order to better show their features and operation.

FIG. 4A illustrates a cross sectional view of a wicking post being filled with allergen transported from filling wells on the planar allergen filling device; FIG. 4B illustrates the filled wicking post;

FIG. 5 shows a perspective view of a planar allergen filling device including arrays of filling wells and associated wicking posts;

FIG. 8A shows a closeup cross section of a fillable allergen site on an allergen-loadable microneedle cartridge aligned with a filled wicking post prior to allergen transfer.

FIG. 11B illustrates the microneedle cartridge deployed toward respective filled wicking posts to transfer allergen;

FIGS. 12A, 12B, and 12C illustrate the dosing of a subject's skin by a microneedle cartridge with an allergen transfer layer design;

FIG. 13C illustrates a spacer placed under a microneedle, supporting associated fillable allergen sites;

FIGS. 15B, 15C, and 15D illustrate how the compressive cartridge unit may dose a subject's skin;

FIGS. 17A, 17B, 17C, 17D and 17E show a number of entrainment microneedle designs with integral fillable allergen sites that may be loaded with allergen extracts as shown in FIG. 16;

FIGS. 19A and 19B illustrate an embodiment that verifies effective filling of planar allergen filling devices using a computer system having a touchscreen display;

FIGS. 20A and 20B illustrate how the system shown in FIGS. 19A and 19B may be operated to verify effective filling of planar allergen filling devices;

FIGS. 21A and 21B illustrate another embodiment that verifies effective filling of planar allergen filling devices using a system that monitors electrical conductivity of filled wicking posts;

FIGS. 22A and 22B illustrate another embodiment that optically verifies effective filling of wicking posts with allergen extracts.

DETAILED DESCRIPTION

Minimally Invasive Allergy Test System

Figure 1:
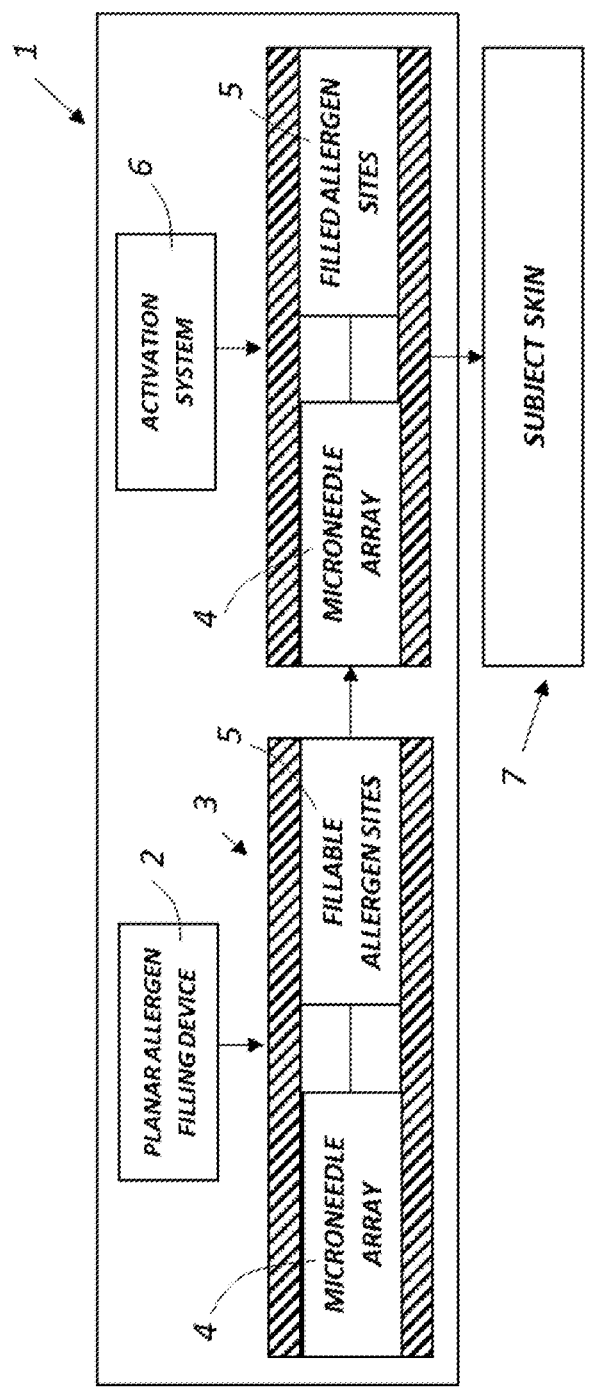
FIG. 1 is a flow chart diagramming embodiments and flow of a minimally invasive allergy testing system.

FIG. 1 illustrates various elements of a minimally invasive allergy test system 1. Depending on the particular system, it may include one or a combination of: a planar allergen filling device 2; an allergen-loadable microneedle cartridge 3 having: a plurality of microneedles 4; entrainment structures integrated with the microneedles or at least one layer with fillable allergen sites 5 comprised of permeable hydrophilic regions associated with the microneedles. In one example, the microneedles are spaced one to fifteen millimeters apart. The spacing and arrangement of microneedles may define a layout which in turn defines a plurality of allergy test sites. In spite of the tight spacings between allergy test sites, the planar allergen filling device 2 disclosed herein allows reliable and accurate filling of fillable allergen sites using, for example, standard eyedroppers or pipettes. As will be described later, the filling process may be done in one scenario assisted by a graphical user interface, minimizing possibility of human placement error. The microneedle cartridges can typically be used with an activation system 6, which deploys and presses a filled allergy test cartridge onto the subject's skin. There is a great degree of flexibility in configuring the activation system. In some embodiments, the activation system 6 can be a mechanical plunger or other mechanical system, which is pressed by a medical professional or even by the test subject. In other embodiments, the activation system 6 can comprise a spring-loaded compressible system which applies a controlled force to the microneedle cartridge as it pricks subject skin 7. The activation system 6 may also comprise a solenoid, a motor, a micromechanical actuator, or another suitable electro-mechanical system that would be available to those skilled in the art.

Planar Allergen Filling Device

Figure 2:
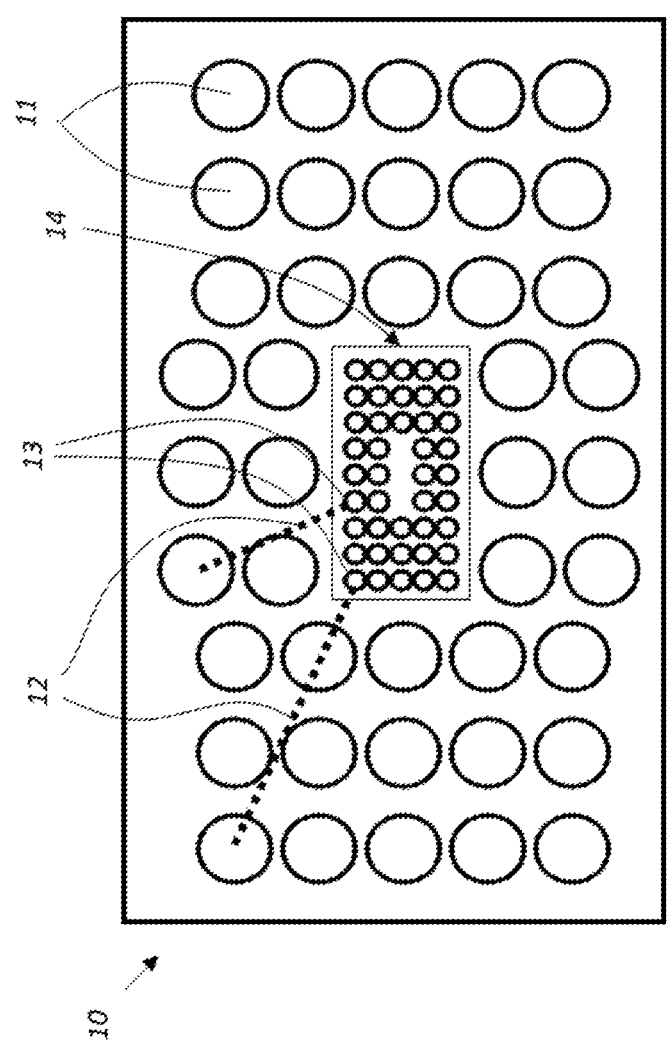
FIG. 2 is a top view of a planar allergen filling device.

FIG. 2 schematically illustrates one example of a planar allergen filling device 10. Filling wells 11 have an allergen deposition area sufficiently large to be reliably and accurately filled manually using, for example, standard eyedroppers or pipettes. Once filling wells 11 are filled, they provide input to capillary channels 12 which transport allergens from each filling well to corresponding allergen loading sites comprised of "wicking posts" 13 located in loading section 14. Depending on their particular structure, such channels may transport allergens through capillary action, diffusion, or other physical mechanisms. Wicking posts 13 are spaced to match the microneedle layout. Once allergens are transported to their respective wicking posts 13, said allergens migrate to the tips of wicking posts 13, to facilitate allergen loading of corresponding fillable allergen sites on the microneedle cartridge. The example illustrated in FIG. 2 includes forty-two filling wells 11 (fillable with allergens and positive/negative controls) and an equal number of wicking posts 13 in loading section 14. It should be noted that depending on their number, placement, and design, many options for positions of filling wells are possible.

Figures 3A, 3B:
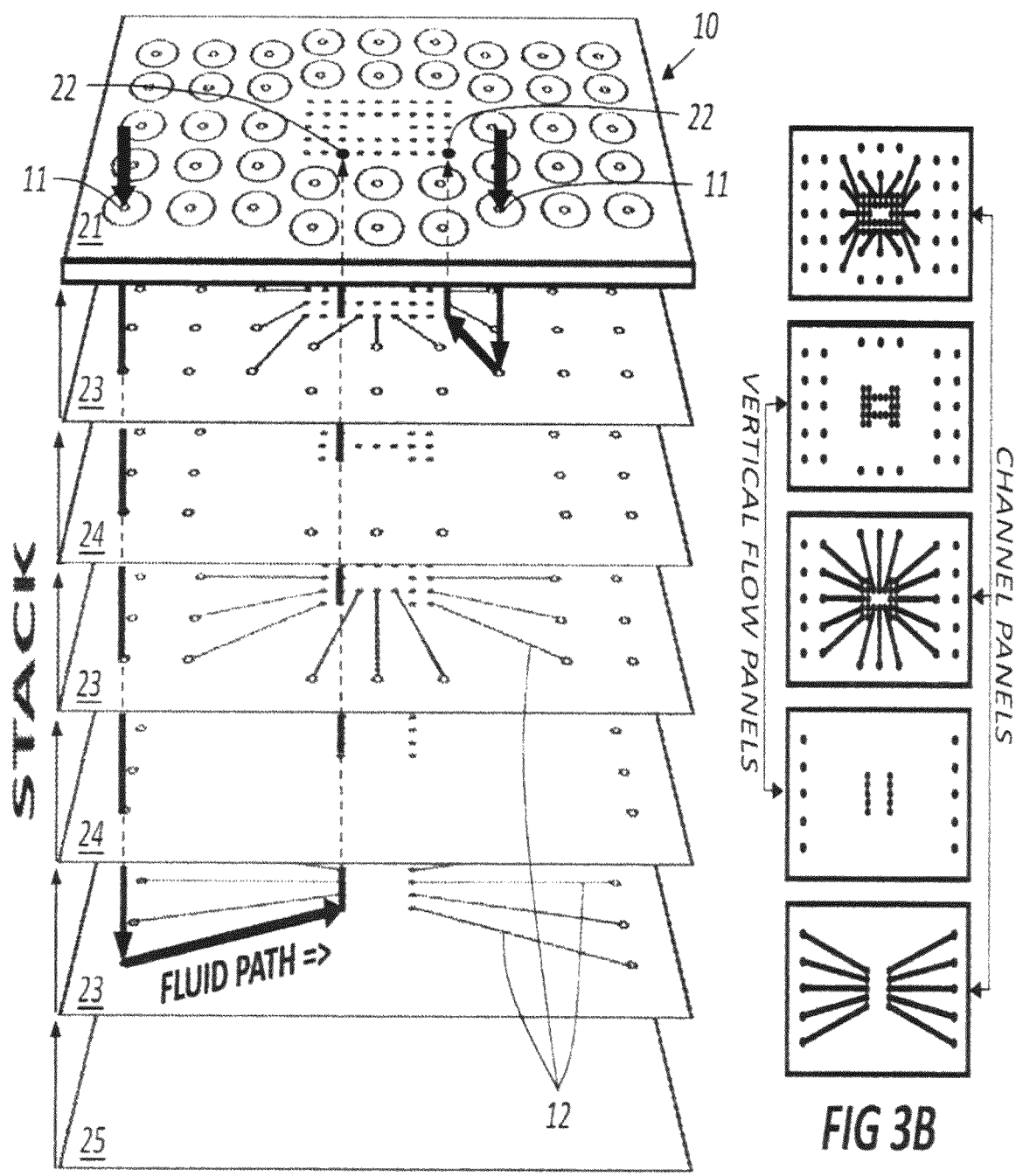
FIG. 3A illustrates an exploded perspective view of a particular embodiment of the planar allergen filling device.
FIG. 3B illustrates a top view of selected panels of the planar allergen filling device.

FIG. 3A illustrates an exploded view of one embodiment of the planar allergen filling device 10. In this embodiment, the top panel 21 is a rigid substrate made of transparent material such as plastic or glass having an approximate thickness of 1-10 millimeters to achieve mechanical stability, rigidity, and an allergen volume at least sufficient to fill wicking posts 13. Filling wells 11 may be tapered, decreasing in diameter versus depth, to effectively reduce the width of capillary channels 12 that they feed. In addition to filling wells 11, top panel 21 includes conduit holes 22 that house wicking posts 13 (not shown here). As will be illustrated later, once allergens come in contact with the wicking posts 13 within the conduit holes 22, said allergens will flow by wicking action to their tips, allowing transfer of allergen to corresponding allergen loading sites of the microneedle cartridge (Although wicking and capillary action are often used interchangeably to describe the same physical phenomenon, the term "wicking" is used herein in connection with the wicking posts and the term "capillary action" is used herein in connection with the channels for clarity).

The exploded view of planar allergen filling device 10 illustrated in FIG. 3A includes a stacked assembly of panels that cooperatively transport allergen from filling wells 11 to corresponding conduit holes 22. Channel interior panels 23 define at least a portion (e.g., side walls) of capillary channels 12 in fluidic communication with filling wells 11 that transport allergen from filling wells to their respective conduit holes 22 (examples of fluid paths from filling wells to conduit holes are shown in FIG. 3A). Vertical flow interior panels 24 effectively block or pass allergen across at least a portion of the thickness of the planar allergen filling device 10. FIG. 3B illustrates a possible embodiment of panels 23 and 24 for a planar allergen filling device that can accommodate a cartridge with forty-two microneedles. In the example illustrated, allergens (it being understood that positive/negative controls may also be included) can be deposited in forty-two filling wells 11 for transport to respective conduit holes 22. To facilitate rapid and reliable transport of allergens from filling wells 11 to conduit holes 22, various parts of the respective panels, e.g., the bottom surface of top panel 21 and vertical flow panels 24, may be hydrophilic, thereby enabling capillary flow through capillary channels 12. Panels 21, 23, 24, and bottom sealing panel 25 may be adhered or fused together to avoid leakage and crossover flow across channels.

FIG. 4A illustrates a cross sectional view of a wicking post 13 within a conduit hole 22. A number of stacked panels 31 create capillary channels 32 that transport allergens from each filling well to the base of a corresponding wicking post 13. In the embodiment illustrated in FIG. 4A, capillary channel 32 transports the allergen by capillary flow to wicking post 13. The bottom sealing base panel 25 illustrated in FIG. 4A is continuous across the entire planar allergen filling device. Wicking post 13 is permeable, wicking the allergen 34 from the base of the wicking post upward toward the tip of wicking post 13. FIG. 4B illustrates the wicking post 13 filled completely with allergen 35.

Wicking posts 13 can be made of hydrophilic fibers (e.g. cotton), cellulose, foam (e.g. polyurethane), contiguous particulate structures and should preferably be mechanically pliable when pressure is applied. In some cases, it may be desirable to include an embedded rigid post within wicking post 13 to increase its mechanical strength and decrease the required amount of allergen required to fill the wicking post.

FIG. 5 illustrates a planar allergen filling device 10 including an array of wicking posts 42 in loading section 41. In this embodiment, wicking posts 42 slightly protrude above the plane defined by the top surface of top panel 21 to enable contact with fillable allergen sites on the allergen-loadable microneedle cartridge.

Allergen-Loadable Microneedle Cartridge with Discrete Fillable Allergen Sites

Figure 6A:
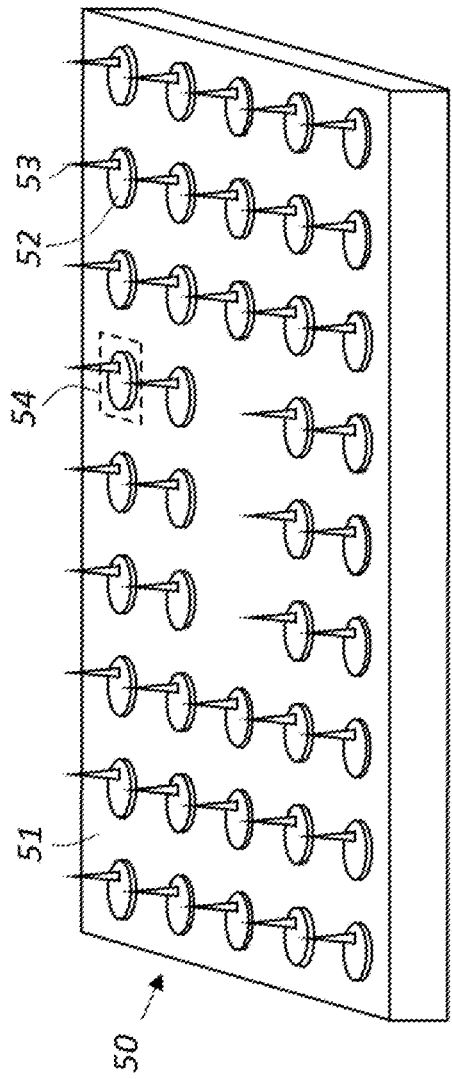
FIG. 6A shows a perspective view of an allergen-loadable microneedle cartridge including fillable allergen sites and associated microneedles.

FIG. 6A illustrates an embodiment for an allergen-loadable microneedle cartridge 50. In this embodiment, substrate 51 supports fillable allergen sites 52 along with microneedles 53 situated within each fillable allergen site. Fillable allergen sites 52 and microneedles 53 define allergy test sites 54, that may be used to test the subject's allergic reaction to specific allergens. The number of allergy test sites 54 on microneedle cartridge 50 determines the maximum number of allergens and positive/negative controls that may be used during a test. It should be noted that the shape and position of fillable allergen sites 52 and microneedles 53 included in allergy test sites 54 may vary, as illustrated in examples depicted in FIG. 6B.

Fillable allergen sites 52 may be composed of one or more layers of hydrophilic absorbing material (e.g. cotton, cellulose-based films, polyurethane foam, particulate structures or other suitable materials that would be accessible to those skilled in the art), be somewhat compressible when pressure is applied, be chemically inert, and able to absorb allergen extracts via capillary action. The thickness, porosity, and compressibility of fillable allergen sites 52 play a role defining allergen dose as the microneedle pricks the subject's skin. The surface of substrate 51 may comprise a hydrophobic substance to hinder allergen flow outside the allergen sites and minimize risk of cross contamination between test sites.

It will be appreciated that for purposes of clarity, microneedles 53 are not drawn to scale in order to better illustrate them in the figure. Microneedles will generally, but not necessarily, extend above the height of the fillable allergen sites 52, depending on various factors, including the degree of compressibility of filled allergen sites 52, the overall length of microneedles 53, and desired penetration of the microneedle into the subject's skin. Microneedles 53 are preferably sufficiently robust to avoid breakage and fine enough at the tip to allow easy insertion into the subject's skin. The array of microneedles as illustrated in FIG. 6A may be manufactured as an integral part of substrate 51 or be individually inserted/molded into the substrate. Microneedles may be fabricated from metal, silicon, quartz, and other biocompatible materials using a number of processes known in the art, such as microfabrication, laser, or chemical etching.

Figure 7:
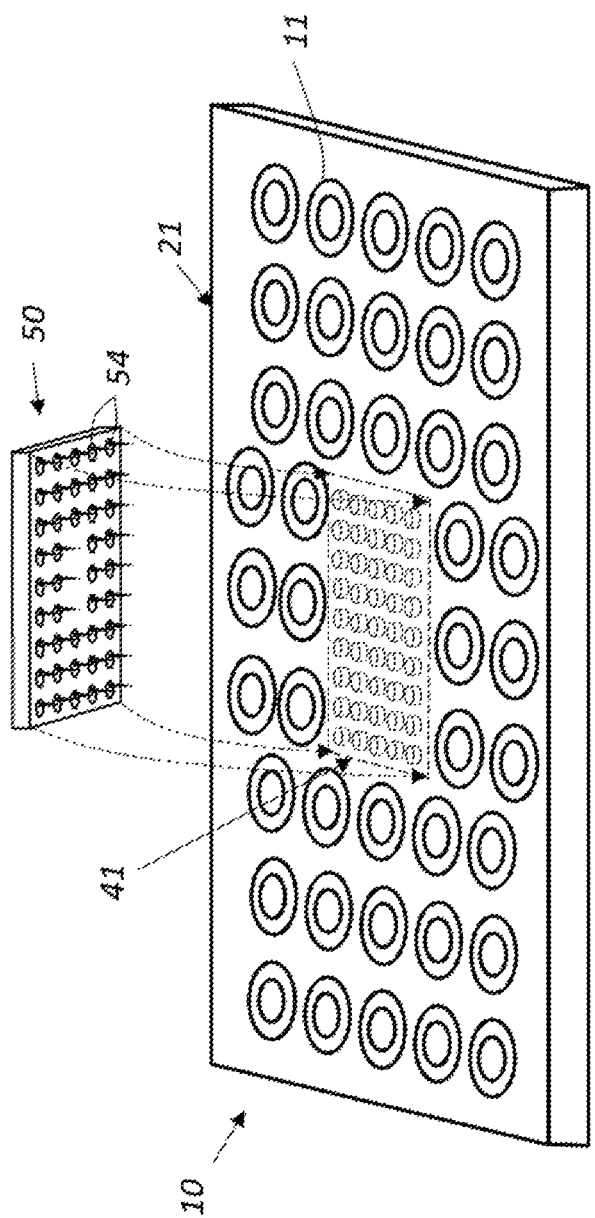
FIG. 7 illustrates the filling of an allergen-loadable microneedle cartridge using a planar allergen filling device.

Allergen Filling Process of an Allergen-Loadable Microneedle Cartridge Having Discrete Fillable Allergen Sites Using a Planar Allergen Filling Device FIG. 7 illustrates a method to fill allergen-loadable microneedle cartridges 50 using the Planar Allergen Filling Device 10. Microneedle cartridge 50 is deployed toward planar allergen filling device 10, e.g., by an activation system such that wicking posts 41 are aligned with corresponding allergy test sites 54 on the cartridge. FIG. 7 shows a perspective view to illustrate the placement of the microneedle cartridge 50 on the array of wicking posts 41. In practice, surfaces of the microneedle cartridge 50 and planar allergen filling device 10 could be parallel, allowing a mechanical actuator to bring the two items in contact using a linear motion.

Figure 6B:
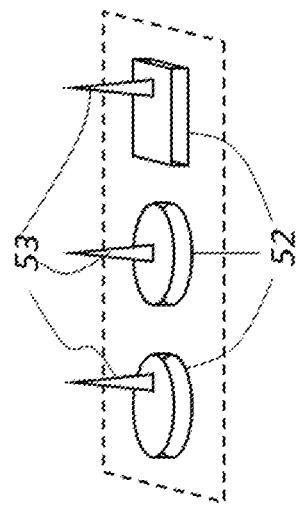
FIG. 6B illustrates three examples of fillable allergen sites and associated microneedles.
Figure 8B:
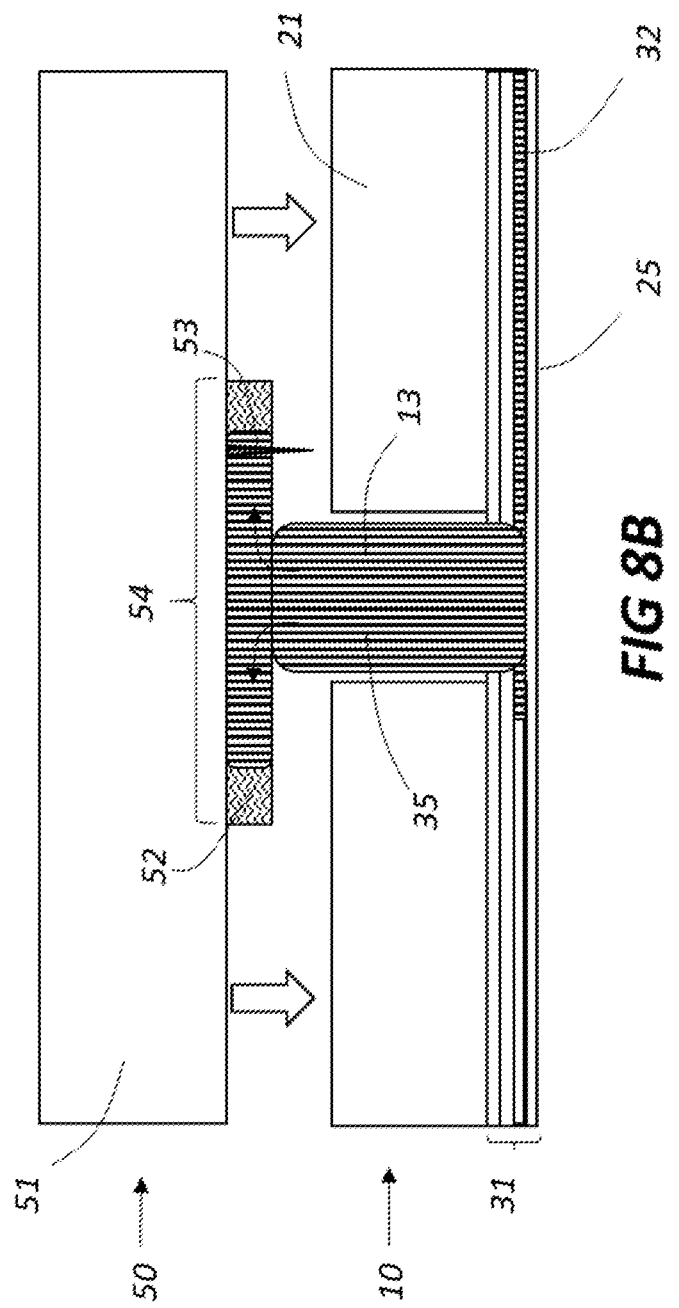
FIG. 8B shows the allergen-loadable microneedle cartridge being filled during allergen transfer.
Figure 9:
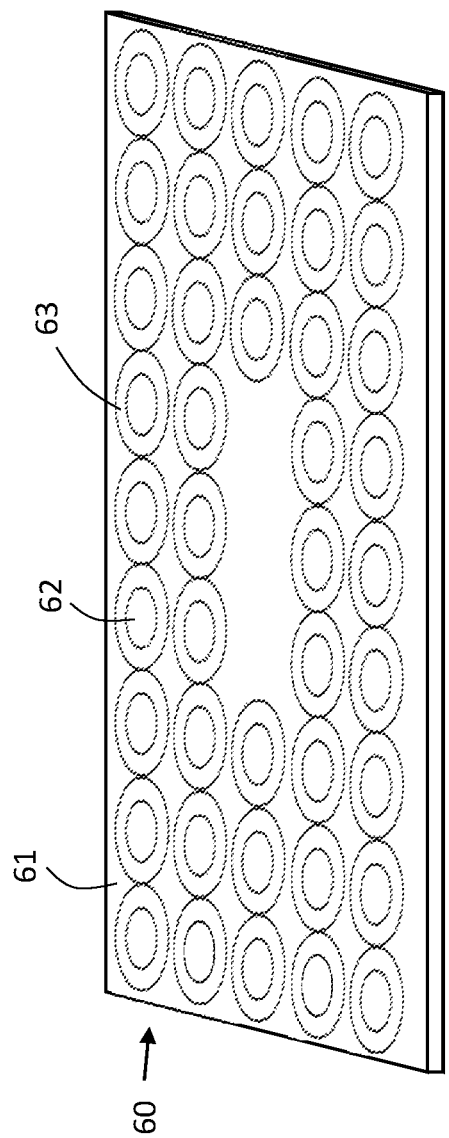
FIG. 9 shows a perspective view of fillable allergen sites, part of a fillable allergen layer, surrounded by moats that hinder allergen flow outside the fillable allergen sites.

FIG. 8A illustrates a closeup cross section of a fillable allergen site 52 aligned with a filled wicking post 13 in preparation for allergen transfer. The position of microneedle 53 relative to the fillable allergen site 52 may vary as illustrated in FIG. 6B, but the height and stiffness of the wicking post 13 must be sufficient to avoid contact between microneedle 53 and panel 21. FIG. 8B illustrates the microneedle cartridge 50 deployed toward the planar allergen filling device 10, bringing wicking post 13 into contact with fillable allergen site 52. When contact is achieved, allergen transfers and may migrate radially, filling or at least partially filling site 52. As wicking post 13 becomes depleted of allergen 35, it can get replenished by allergen flow through channel 32 assuming sufficient allergen was deposited in its respective well. In this manner, multiple fillable allergen cartridges may be filled with only one filling of the wells. Although this embodiment illustrates microneedle 53 adjacent to wicking post 13, another embodiment having the microneedle aligned to the wicking post is possible, as long as wicking post 13 can be penetrated by microneedle 53 without breakage or adverse consequences. Although the referenced figures show one needle per site, those skilled in the art will appreciate that additional needles may be included for any or all sites.

Allergen-Loadable Microneedle Cartridge with a Fillable Allergen Layer

Although fillable allergen sites may be discrete elements integrated with a substrate as illustrated in FIGS. 6-8, FIG. 9 illustrates an embodiment where fillable allergen sites 62 are part of a fillable allergen layer 60. Fillable allergen layer 60 may start out as a hydrophilic absorbing layer 61 (e.g.

cotton, cellulose, polyurethane foam, particulate structures, or other appropriate materials that would be accessible to those skilled in the art) with suitable thickness, e.g., 0.1 mm to 3 mm thick, depending on its compressibility, absorptivity, desired test dosage, spacing between test sites, and microneedle geometry. To define the fillable allergen sites 62, "moats" 63 are created around the fillable allergen sites to hinder allergen flow outside the fillable allergen sites 62. Such moats may hinder allergen flow by, for example, being hydrophobic or impermeable relative to other portions of the fillable allergen layer. Formation of the hydrophobic moats may be done by stamping, 3D printing, spraying hydrophobic or other appropriate compounds that will dry or be cured, or by other suitable methods that would be accessible to those skilled in the art.

Figure 10A:
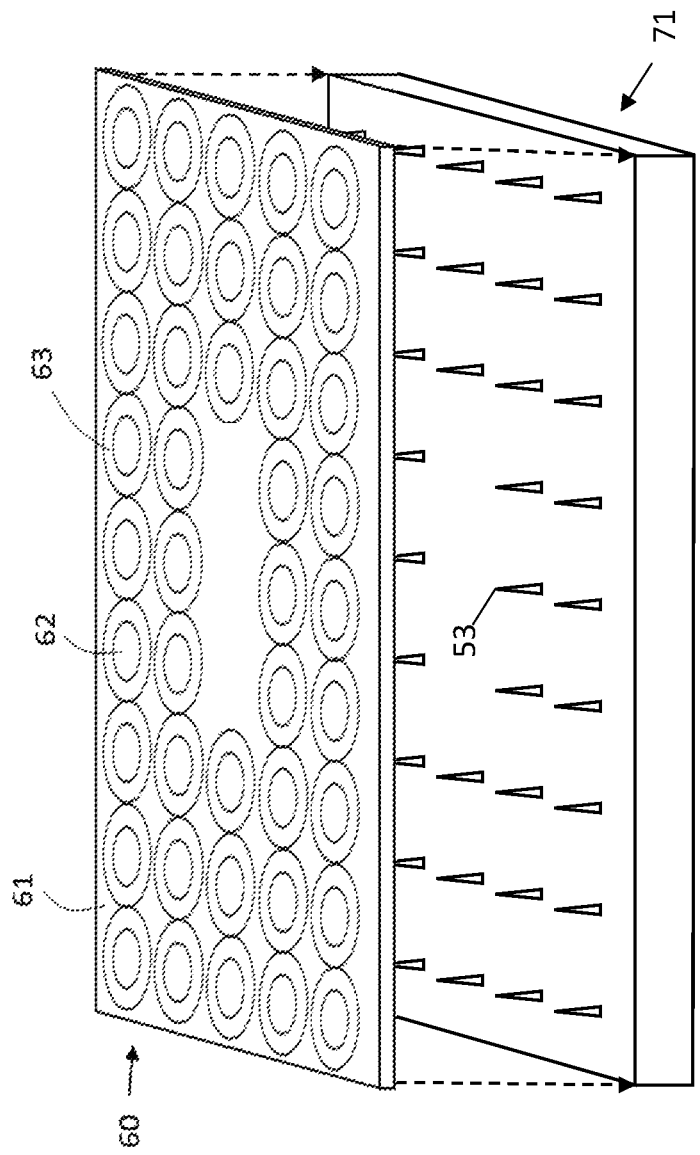
FIGS. 10A and 10B illustrate the fillable allergen layer of FIG. 9 being coupled and integrated onto a microneedle array.
Figure 10B:
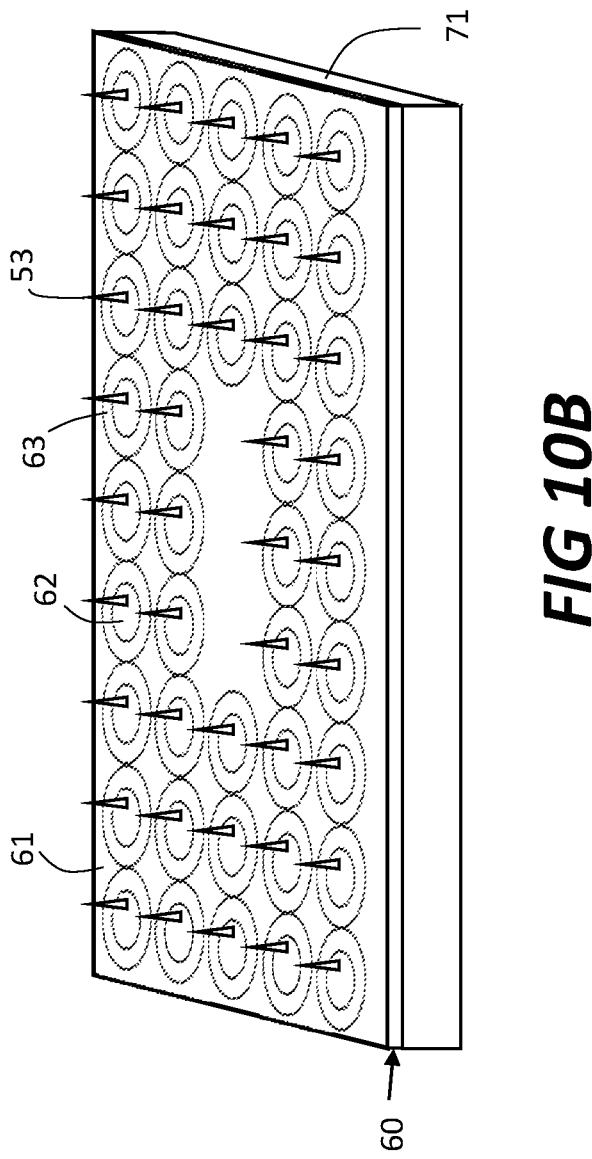

FIG. 10A illustrates how the fillable allergen layer 60 (prior to wicking with allergen) may be coupled to a microneedle array 71. The layout and spacings of the fillable allergen sites 62 are designed to match the layout and spacings of microneedles 53, allowing each microneedle 53 in array 71 to penetrate the corresponding allergen site 62 in the fillable allergen layer 60 as illustrated in 10B. Since the thickness of the fillable allergen layer will effectively decrease the height of the microneedles, its thickness (and compressibility) should be considered to achieve the desired penetration into the subject's skin. In certain embodiments, adjacent surfaces of the microneedle array 71 and fillable allergen layer 60 may be adhered after positioning for mechanical stability. In other embodiments, such as a compressible cartridge (to be described), the microneedle array 71 and fillable allergen layer 60 may not be adhered in order to impart certain other attributes to the cartridge.

Figure 11A:
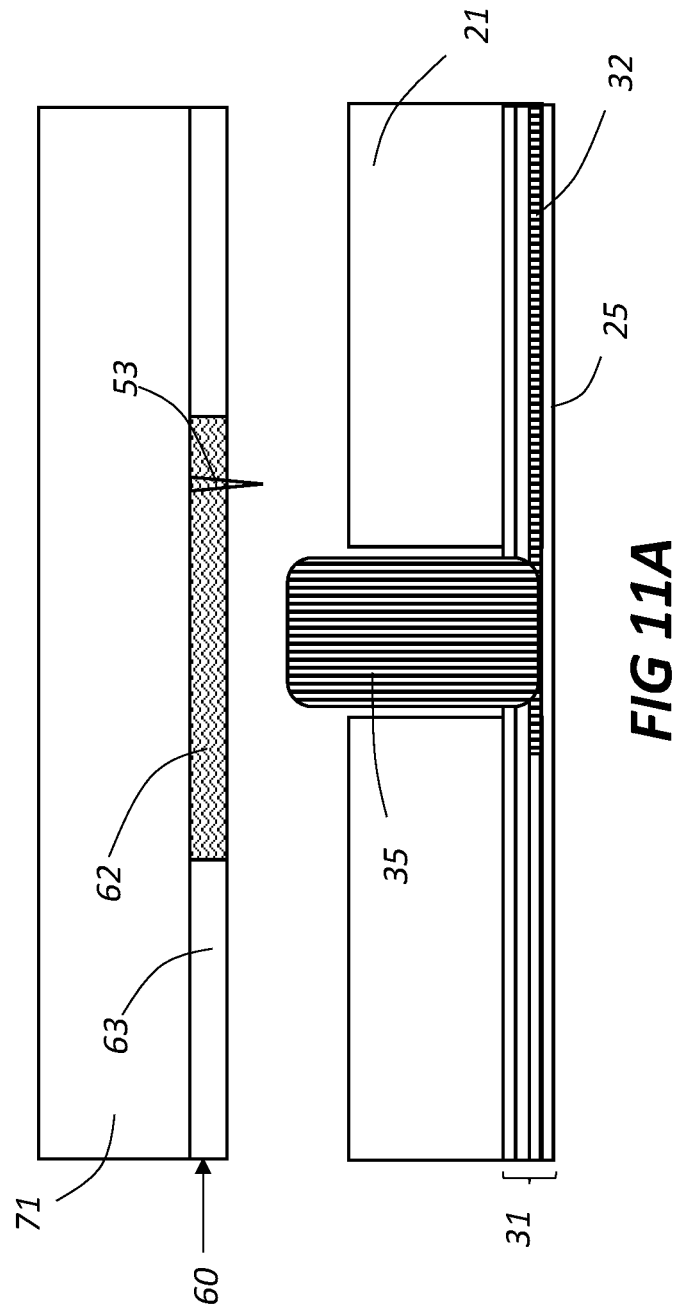
FIG. 11A illustrates a cross section of a microneedle cartridge supporting a fillable allergen layer in preparation for allergen transfer.

Allergen Filling Process of an Allergen-Loadable Microneedle Cartridge Having a Fillable Allergen Layer Using a Planar Allergen Filling Device In one embodiment employing an allergen transfer layer, allergens may be loaded into the cartridge in a similar manner as illustrated in FIG. 8B. FIG. 11A illustrates a cross section of a microneedle cartridge 71 supporting a fillable allergen layer that includes a hydrophilic fillable allergen site 62 aligned to a filled wicking post 13 in preparation for allergen transfer. In this example, wicking post 13 was filled with allergen 35 through channel 32. Fillable allergen site 62 surrounded by hydrophobic moat 63 is aligned with wicking post 13 to initiate allergen transfer. FIG. 11B illustrates the microneedle cartridge 71 being deployed toward the planar allergen filling device 21, bringing wicking post 13 in contact with fillable allergen site 62. When contact is achieved, due to the hydrophilic nature of the fillable allergen site 62, allergen transfers and migrates radially until reaching the boundary of hydrophobic moat 63. As wicking post 13 becomes depleted of allergen 35, it can get replenished by allergen flow through channel 32 assuming sufficient allergen was deposited in its respective well. In this manner, multiple fillable allergen cartridges may be filled with only one filling of the wells. Although this embodiment illustrates microneedle 53 adjacent to wicking post 13, another embodiment having the microneedle aligned to the wicking post is viable, assuming wicking post layers made of hydrophilic and/or absorbing material, e.g. cotton fiber, cellulose, foam (e.g. polyurethane) or other suitable materials that would be accessible to those skilled in the art, can be penetrated by the microneedle.

Allergy Test Dosing

Figure 12A:
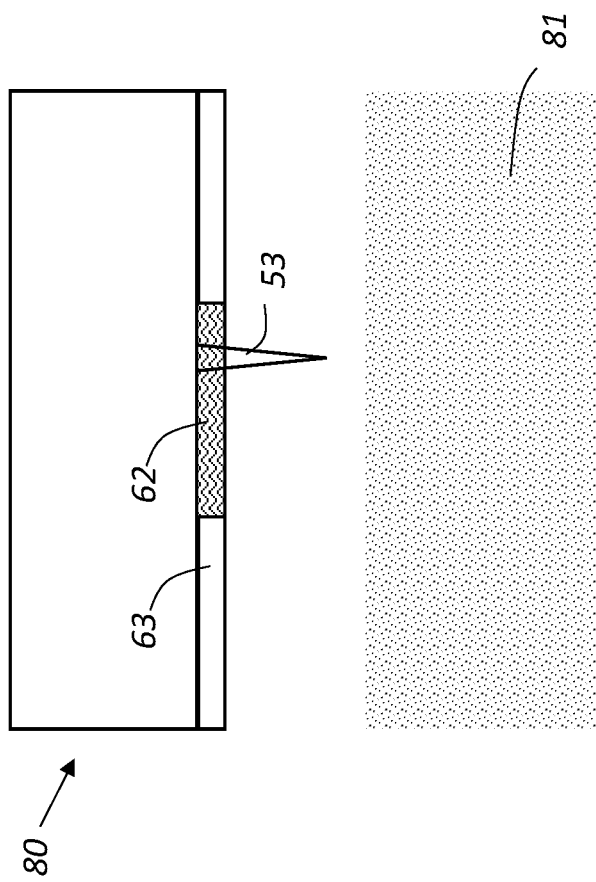
Figure 12B:
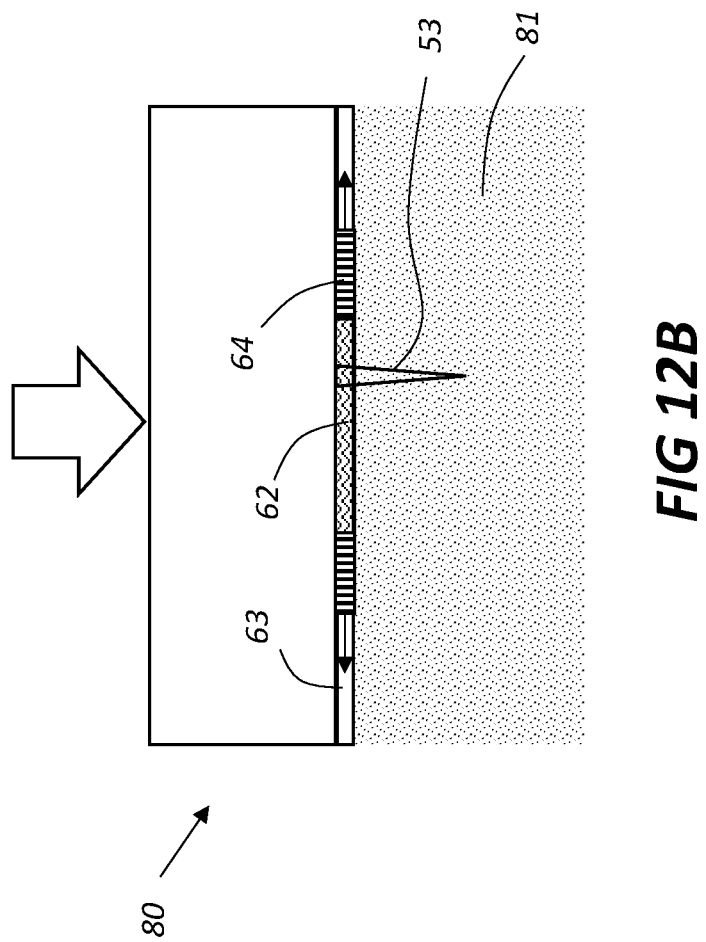

FIG. 12A and FIG. 12B illustrate a cross section view of how a subject's skin may be dosed using a microneedle cartridge with an allergen transfer layer design. It will be appreciated that what is described herein below appears to be the likely mechanism of action but is not a limitation. It will further be appreciated that a microneedle cartridge having discrete fillable allergen sites as illustrated in FIGS. 6-8 may be also be used. For purposes of clarity, the various elements in FIG. 12A and FIG. 12B have not been drawn to scale in order to better illustrate and describe their features and operation.

FIG. 12A illustrates a single needle in a microneedle cartridge 80 prior to subject skin 81 penetration. The illustrated section of cartridge 80 comprises a microneedle 53, a filled allergen site 62, and a hydrophobic moat 63. FIG. 12B illustrates penetration of microneedle 53 into subject's skin 81.

Force applied by the activation system to the microneedle cartridge inserts microneedle 53 into subject skin 81 and brings the filled allergen site 62 in contact with subject skin 81. Continued force on 80 applies pressure between the filled allergen site 62 and the skin 81, wetting the skin with allergen. In certain embodiments, applied pressure that compresses filled allergen site 62 and hydrophobic moat 63, may cause excess allergen 64 to be laterally displaced into hydrophobic moat 63 as illustrated in FIG. 12B. When microneedle cartridge 80 is lifted by the activation system as illustrated in FIG. 12C, microneedle 53 is extracted from subject skin 81, causing surrounding allergen to fill the evacuated prick hole 66 (volume vacated by the microneedle) also leaving a region of allergen-wetted skin 65. As a result of the hydrophobicity of moat 63, laterally displaced allergen 64 that entered the hydrophobic moat 63 returns to allergen site 62.

Figure 13A:
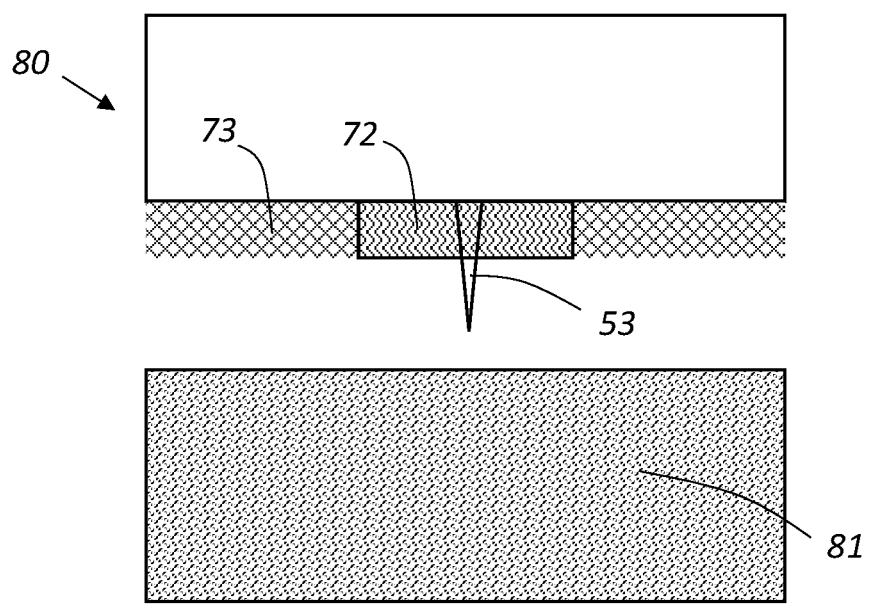
FIGS. 13A and 13B illustrate an embodiment of hydrophobic moats made of a largely incompressible 3D lattice network hydrophobic moat being pressed onto the subject skin.
Figure 13B:
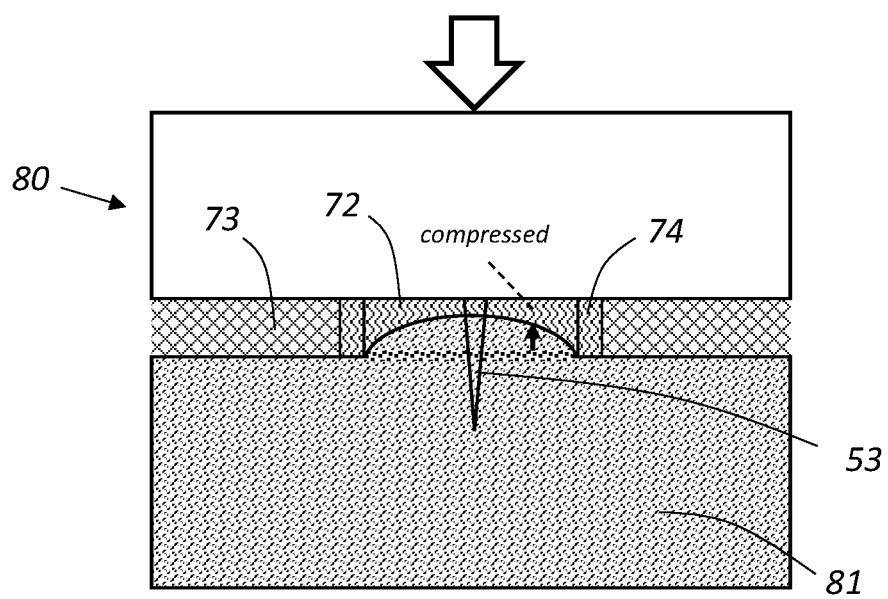

Another embodiment of hydrophobic moats 63 is illustrated in FIG. 13A. In this embodiment, the hydrophobic moat 73 is a rigid 3D lattice network that does not significantly compress when force is applied when compared to allergen fillable site 72. Although the hydrophilic allergen site 72 may be compressed by subject skin 81 as illustrated in FIG. 13B, since the thickness of the hydrophobic moat 73 remains relatively constant, the radius of penetration of excess allergen 74 into hydrophobic moat 73 is minimized compared to what is illustrated in FIG. 12B. Reduced radii of allergen penetration into hydrophobic moats 73 will reduce potential cross-contamination between test sites and allow closer spacing between allergy loading sites.

As illustrated in FIG. 13C, a spacer 91 may be included under the microneedle to further control dosing by making the process less dependent on the Young's Modulus of the skin.

Compressible Allergen-Loadable Microneedle Cartridge

Figure 14A:
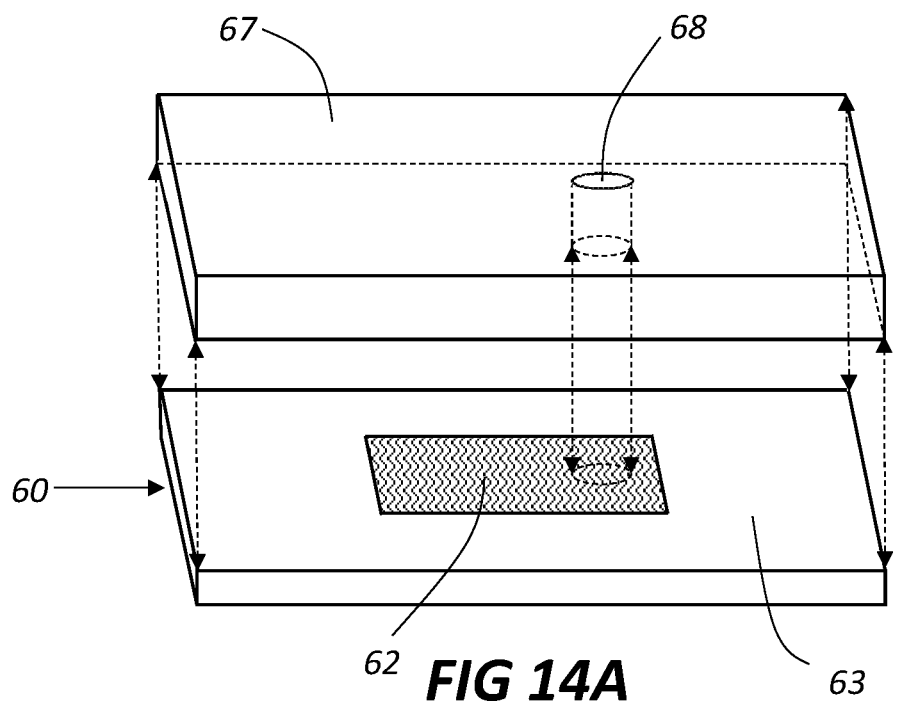
FIGS. 14A and 14B show perspective views of a fillable allergen layer being coupled to a rigid substrate.
Figure 14B:
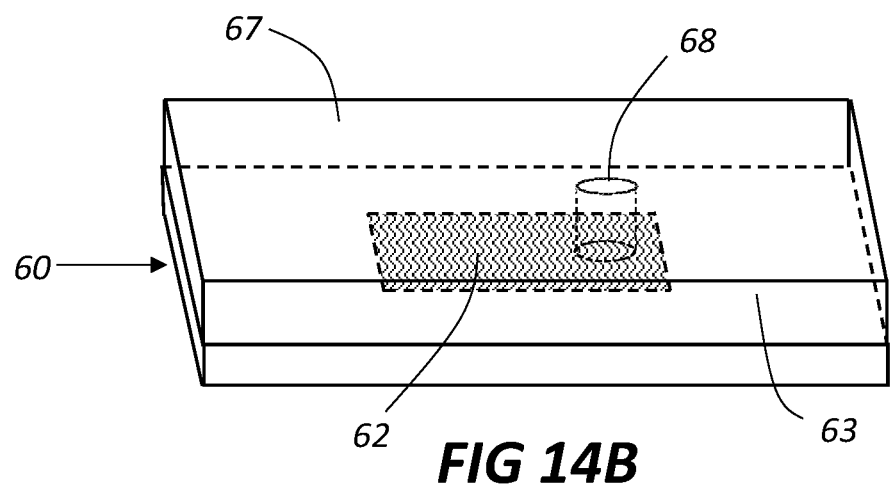

The allergen-loadable microneedle cartridges thus far described integrate fillable allergen sites, hydrophobic moats, and microneedle arrays into a single element. As previously noted, adjacent surfaces of the microneedle array 71 and fillable allergen layer 60 may be adhered or fused together for mechanical stability. Other embodiments, however, may include additional elements to modify its operation. For example, FIG. 14A shows an exploded perspective view of a fillable allergen layer 60 including fillable allergen sites 62 and hydrophobic moats 63 residing on a rigid substrate 67 instead of a microneedle array. Rigid substrate 67 includes holes 68 that provide pathways for microneedles residing on a separate substrate to fillable allergen sites 62 and ultimately the subject's skin. FIG. 14B shows the fillable allergen layer 60 integrated onto the rigid substrate 67.

Figure 15A:
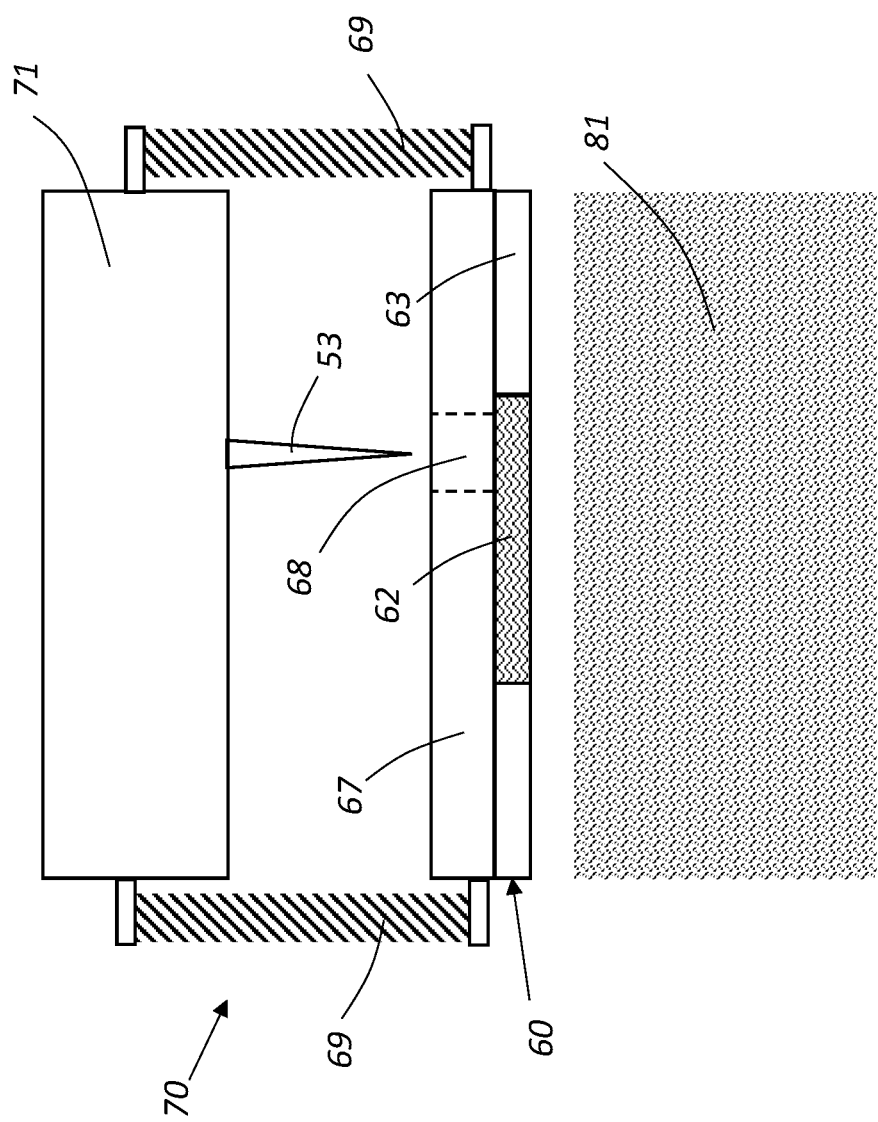
FIG. 15A shows a cross section view of a compressible cartridge unit including a fillable allergen layer as shown in FIG. 14B separated from a microneedle array.
Figure 15B:
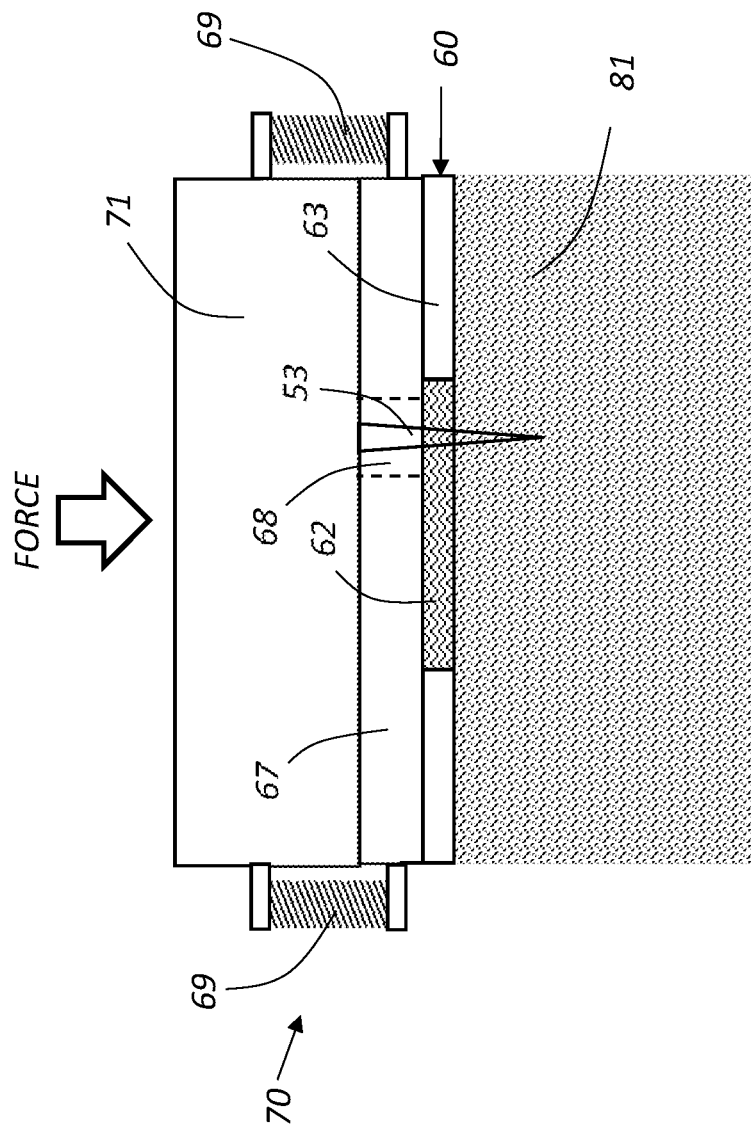
Figure 15D:
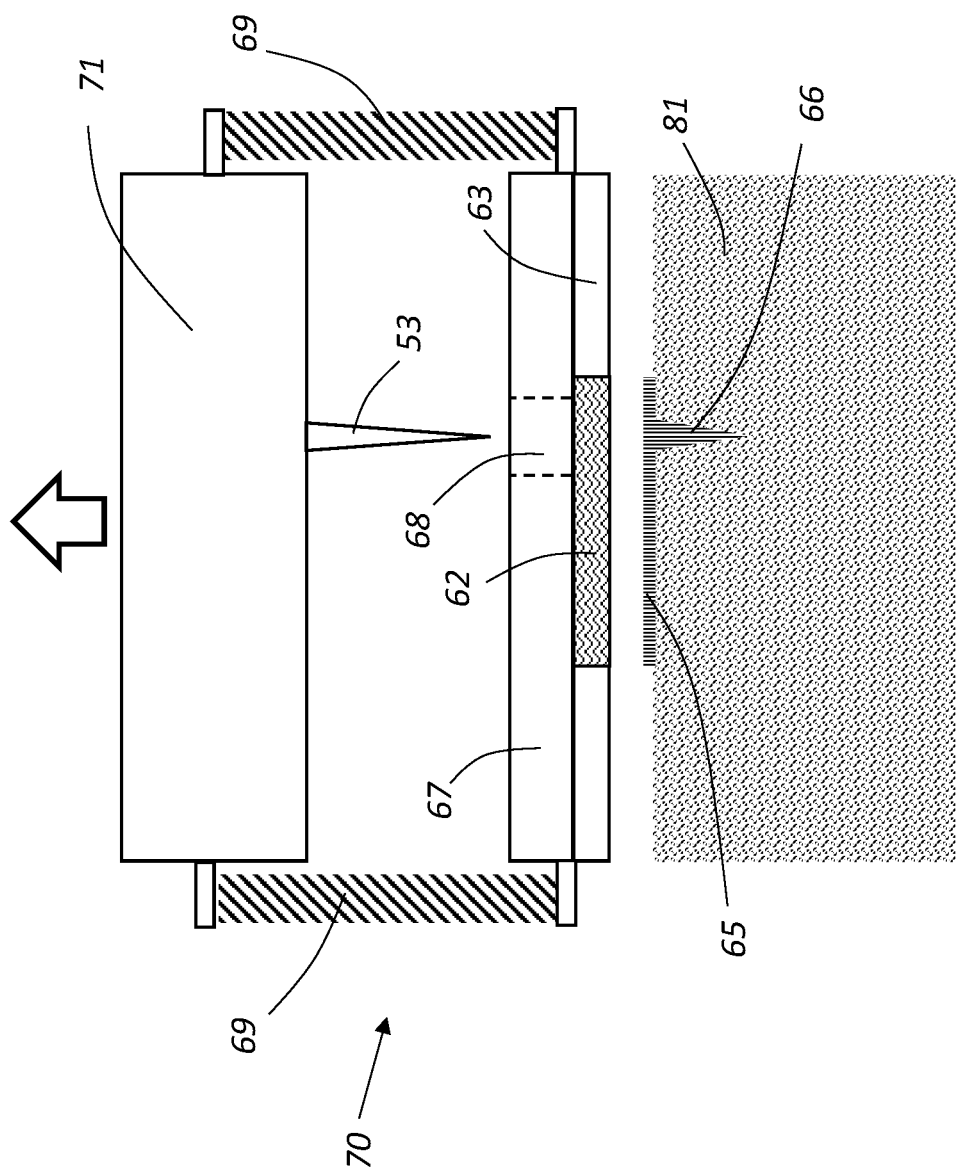

FIG. 15A shows a compressible cartridge unit 70 including a fillable allergen layer 60 residing on rigid substrate 67, supported and separated from a microneedle array 71 by compressible elements 69. Compressible elements 69 may be springs, compressible foam, or any other element that undergoes compression when a force is applied. Microneedles 53 on microneedle array 71 are positioned in alignment with holes 68 so they can pass through said holes to reach fillable allergen sites 62 and ultimately prick subject skin 81. As force is applied to compressible cartridge 70 toward subject skin 81, the fillable allergen layer 60 first comes into contact with subject skin 81. As additional force is applied to compressible cartridge unit 70, microneedle 53 passes through hole 68, punctures fillable allergen site 62, eventually puncturing skin 81 as illustrated in FIG. 15B. After penetration (and optionally a short delay, to allow compressible cartridge unit 70 and skin to mechanically settle), the microneedle array is moved away from the subject as illustrated in FIG. 15C. During removal of the microneedle 53 from subject skin 81, fillable allergen sites 62 remain in contact with subject skin 81 for a period of time, thereby facilitating allergen flow into the evacuated prick hole 66 illustrated in FIG. 15C. FIG. 15D shows the completed process after the compressible cartridge returns to its original position, leaving behind region of allergen-wetted skin 65 and the evacuated prick hole 66 dosed with allergen. For purposes of clarity, the various elements in FIG. 14 and FIG. 15 are not drawn to scale in order to better illustrate and describe their features and operation. It will be noted that fillable allergen sites 62 in FIG. 15A may be filled prior to testing in the same manner as illustrated in the examples of FIG. 11A and FIG. 11B, by bringing the filled wicking posts in contact with the fillable allergen sites 62.

Allergen-Loadable Microneedle Cartridge with Entrainment Microneedles

Figure 16:
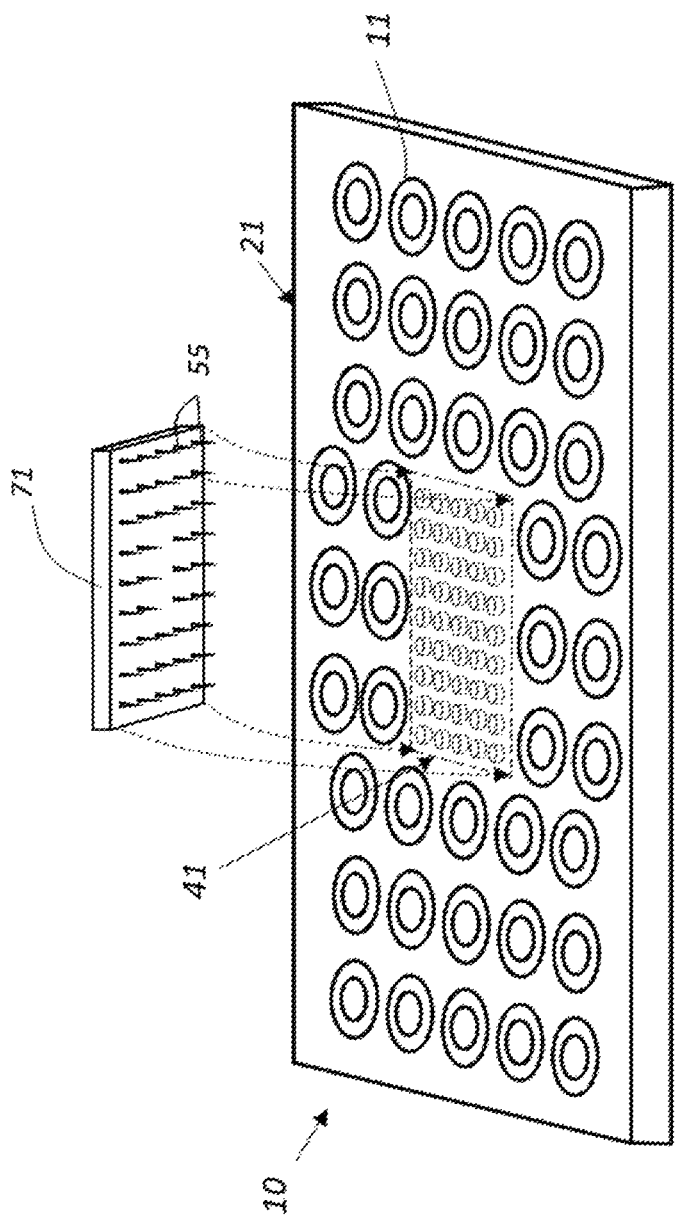
FIG. 16 illustrates a perspective view of an allergen-loadable microneedle cartridge having fillable allergen sites located on entrainment microneedles being loaded with allergen.

The embodiments thus far described involve fillable allergen sites residing on substrates that couple specific allergens with microneedles. In another embodiment of present invention, fillable allergen sites reside directly on entrainment microneedles 55 and may be filled using the planar allergen filling device 10 as shown in FIG. 16. In this embodiment, fillable allergen sites reside in entrainment microneedles 55

FIG. 12C and FIG. 15C, illustrate how allergen flows into evacuated prick holes to dose subject skin when there is a source of allergen extract in the vicinity of the region of the prick hole. Standard smooth microneedles, if coated as shown in FIG. 16, may not provide effective dosage of allergen extracts since inward pressure by subject skin around the perimeter of prick holes tends to extrude fluid extracts outward. Although needles coated with dried allergens may carry allergen into the skin during insertion, allergen extracts considered in the present invention have a low vapor pressure and do not evaporate readily. Given the above, an alternative microneedle design that includes entrainment structures will be presented.

FIG. 17 shows a number of entrainment microneedle designs with integral fillable allergen sites that may be loaded with allergens extracts as shown in FIG. 16 and that allow entrainment of loaded allergen extracts into the subject's skin. FIG. 17A shows entrainment microneedle 56 with either micromachined, injection molded, or laser machined crevices 200 formed in the microneedle surface. If the material of microneedle 56 is sufficiently hydrophilic, crevices will carry a certain volume of allergen extract into subject skin during insertion. In this embodiment, dosage is determined by the allergen concentration of the extract times the effective volume of the crevices that penetrate the skin. Although crevices depicted in FIG. 17A follow the circumference of the microneedle, multiple crevices along its length are also an option. Since crevices will affect microneedle fracture strength depending on microneedle geometry and material, there will be limits to their position, width, and depth to reduce probability of breakage. FIG. 17B shows a related entrainment microneedle 57 having finer crevices in a more randomized pattern.

FIG. 17C shows a standard microneedle 53 coated with an absorbing hydrophilic layer 202 that allows diffusion of the allergen extract into its volume. The effective dose will depend on factors such as its porosity and/or its ability to swell when the allergen extract is absorbed. The layer must be mechanically robust and able to penetrate skin along with the microneedle without fracture or release. Hydrophilic layer material should be largely water insoluble, so it retains its chemical and physical properties during allergen wicking and skin penetration processes. Although preferably the layer should not be water soluble, slow solubility may be acceptable as long as the material is biologically safe and does not affect the allergic reaction. Hydrophilic layer 202 may include film forming agents and binders such as hydropropyl cellulose, ethyl cellulose, carboxymethyl cellulose. Cellulose-based hydrophilic powders or structures shown as 203 in FIG. 17D may also be affixed/adhered to microneedle 53 using water insoluble adhesive thin layers such as cyanoacrylates.

FIG. 17E shows a thin patterned hydrophilic layer 204 coated on microneedle 53 supporting patterned hydrophobic layers 205, forming crevices 206. The spacing and height of the patterned hydrophobic layers 205 must be sufficient to allow entrainment of allergen extract into the skin to achieve the desired dosage. Layer 204 may not be required if microneedle 53 is hydrophilic in nature.

Digital Display System Facilitated Method for Loading Filling Wells

To guide the deposition of allergens into specific filling wells, a planar allergen filling device such as described above may be used in concert with a display system driven by a laptop, tablet, or other computing system that provide a graphical user interface guiding the filling of each allergen loading site. Patient ID, allergen panel, positional information of allergens on the cartridge, date, and other metadata may also be shown by the display. The planar allergen filling device, if transparent or partially transparent, may be placed over the display, allowing the user to view positional markers, allergen ID's/barcode information, and other pertinent information for the test being performed. If the planar allergen filling device is not transparent, a projection system may be used that projects information cited above on the planar allergen filling device properly located relative to the projected screen image.

Figure 18A:
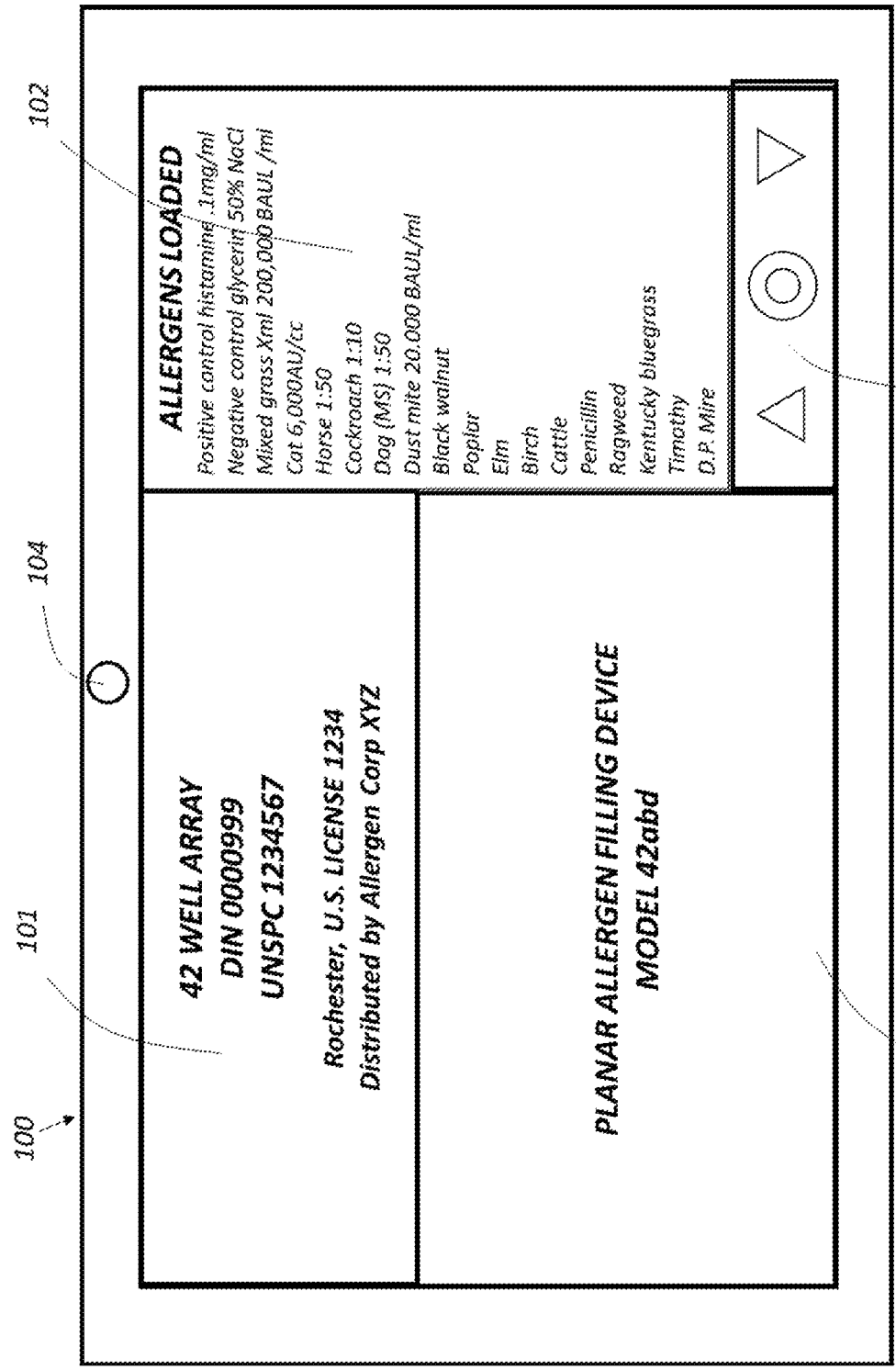
FIGS. 18A, 18B, 18C, and 18D illustrate schematically a display system driven by a laptop, tablet, or other computing system that guides the filling of planar allergen filling devices with allergen extracts.

FIG. 18A illustrates an embodiment for the display system and a method to load the planar allergen filler device. This embodiment includes computing and display system 100 running software that displays: a region 101 identifying the type of planar allergen filler device used; a region 102 defining the allergen panel selected to fill filling wells; a region 103 illustrating where allergens will reside on the cartridge; a control panel 110 to control and monitor the process. To further enable the process, the computing system shown may have a camera/bar code reader 104 along with touch screen capabilities. It should be noted that the software would scale region 103 to dimensionally accommodate the specific planar allergen filling device used.

Figure 18B:
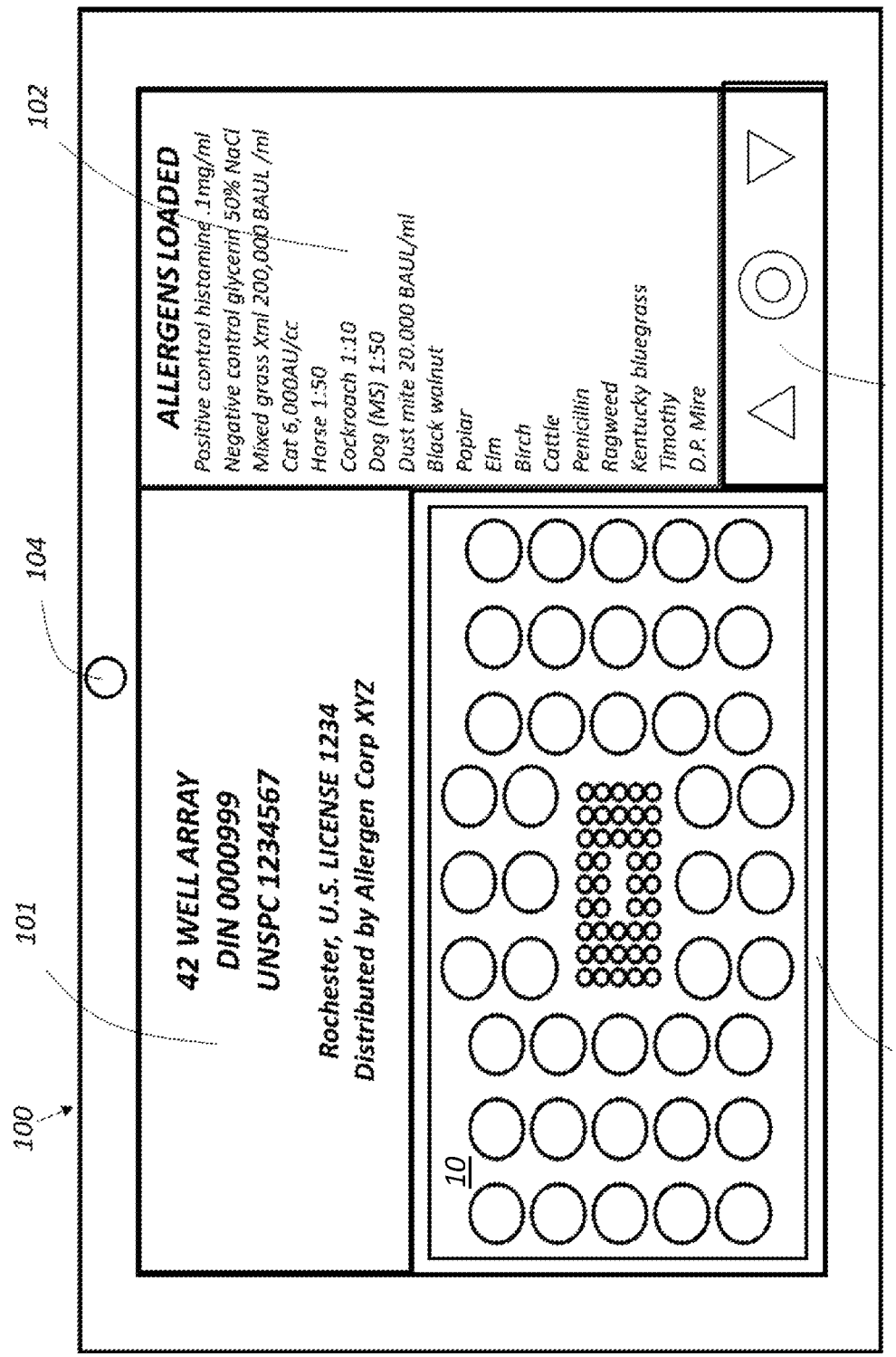

FIG. 18B illustrates a computing and display system 100 carrying a planar allergen filler device 10 which was physically placed on region 103. Region 103 may fit the actual planar allergen filler device to be used or, to reduce risks of contamination, region 103 may fit a sealable transparent planar case that holds the planar allergen filling device (its lid is opened or removed during the allergen loading process). Camera and barcode reader 104 can be used to identify and/or confirm the specific planar allergen filler device being used for the test among other items used. The computing device 100 can provide either audible or visible signals to notify the user of the status of the filling process.

Figure 18C:
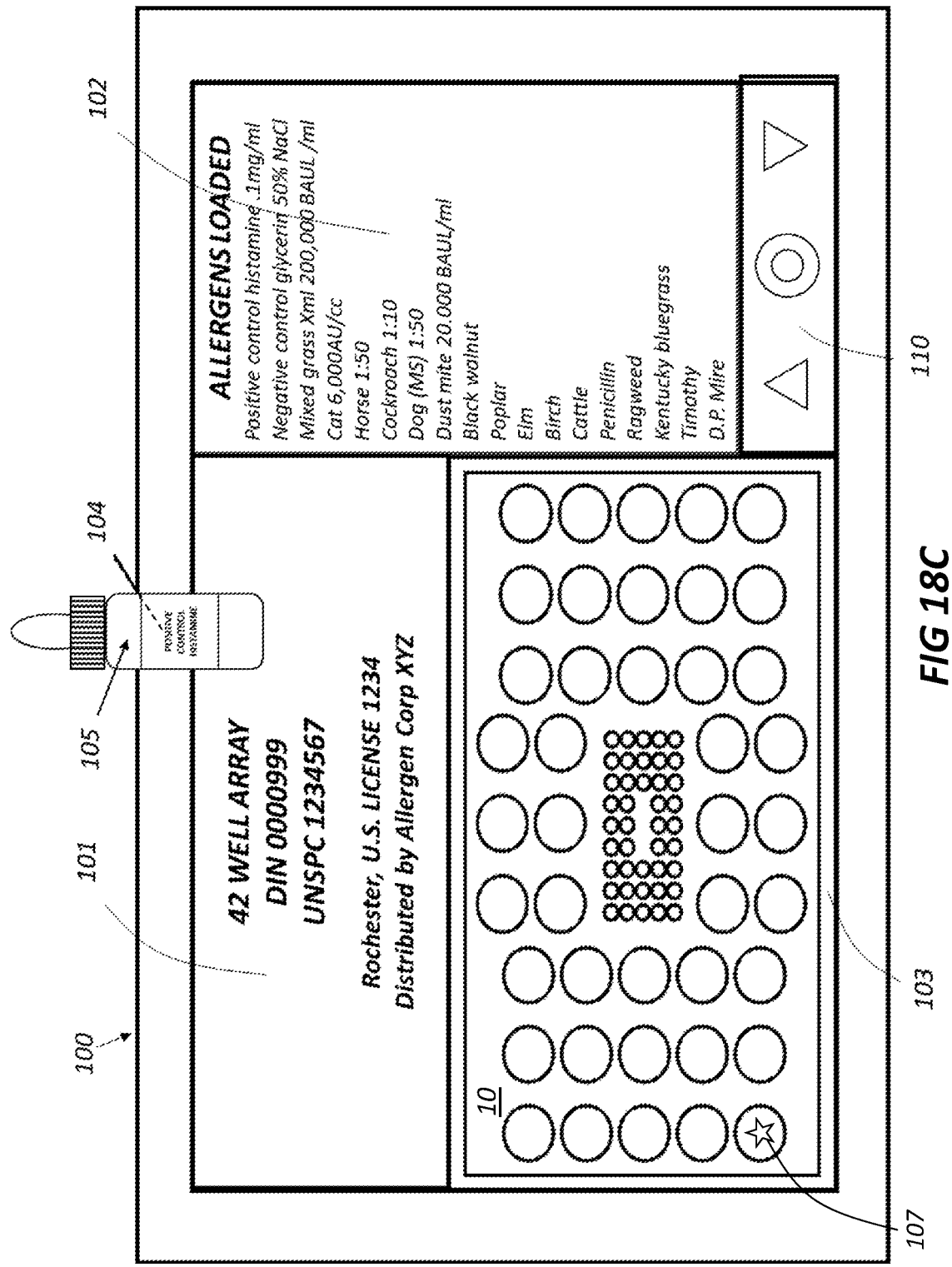

FIG. 18C illustrates how the filling process may proceed. The barcode on a specific bottled allergen extract 105 (in this example, a positive control) is presented to the barcode reader, identified, and highlighted in section 102 of the display. At the same time, the filling well location for the specific allergen extract is identified on the screen (shown as 107). Although FIG. 18C illustrates a star marker under the filling well to be filled, other graphical methods (e.g. bright, colored, flashing regions under the filling well) may be used to identify the specific filling well for allergen extract 105. Once the filling well is filled (typically 3-6 drops) the user can either proceed by presenting another bottle of allergen to barcode reader 104 or use the control panel to continue the process.

Figure 18D:
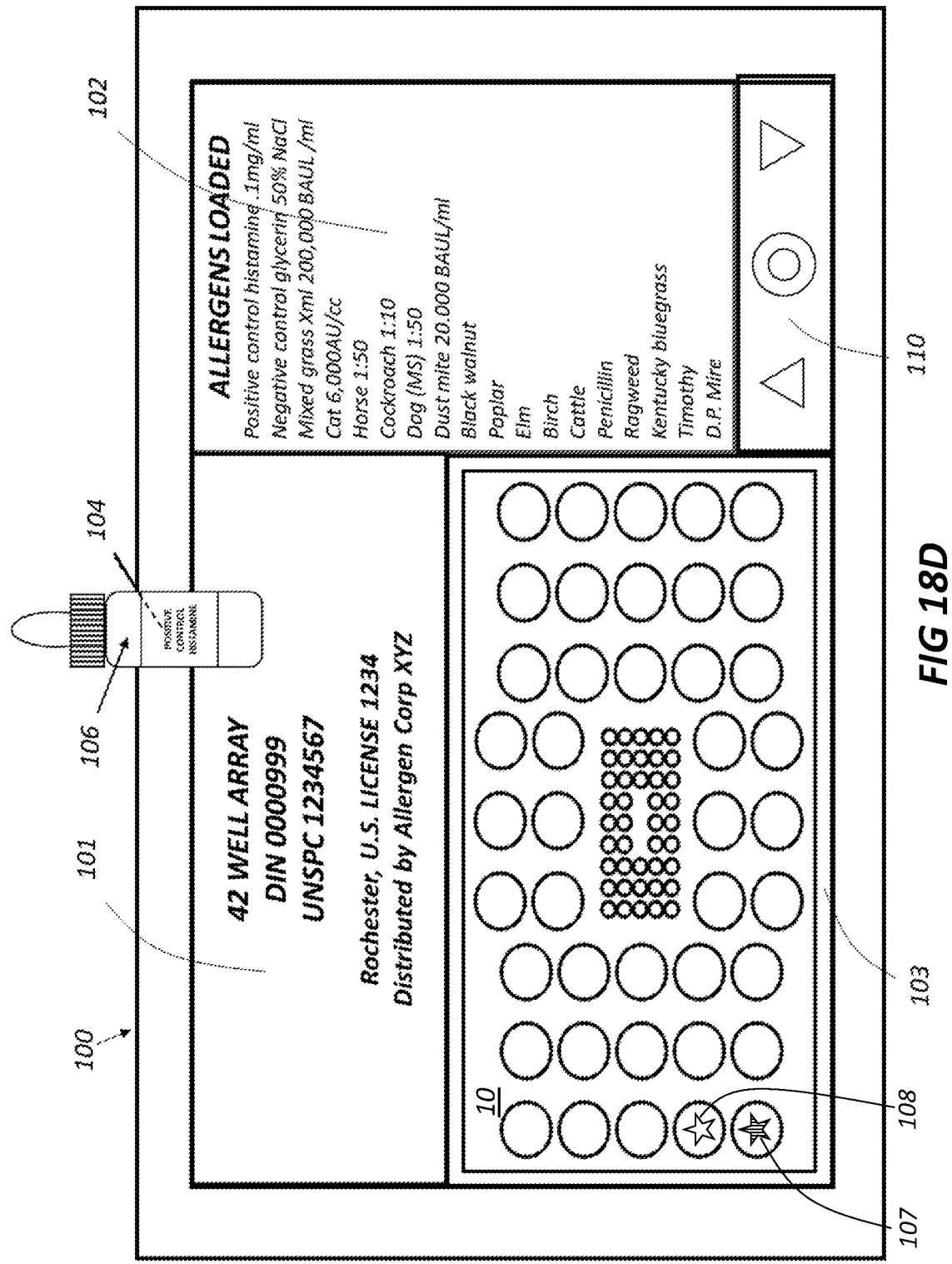

FIG. 18D illustrates a second bottle of allergen extract 106 presented to the barcode reader (highlighted in section 102) and another specific filling well 108 is labelled (with a star 108) in region 103. Color or graphic changes are made both to filling well 107 and the corresponding allergen on list 102 illustrating the allergen has been deposited. The process thus far described for allergen extracts 105 and 106 is repeated for the rest of the panel shown in section 102. It should be noted that the software may be configured to either trigger allergen deposition after reading the barcode on an allergen extract bottle as illustrated in FIG. 18C and FIG. 18D or be listed sequentially allergen by allergen on the list in section 102 to guide the process. The procedure described above may be varied to match specific requirements needed by the user.

A further embodiment of the method thus far described is to utilize a tablet's touchscreen system to verify both allergen deposition and transport processes. FIG. 19A illustrates (as in FIG. 4A) a cross sectional view of a wicking post being filled. Attached under the bottom sealing panel 25 of the planar allergen filling device are small thin pads 110, lightly adhered to region 103 of the tablet's display illustrated in FIG. 18. Each thin pad 110 is aligned to corresponding wicking posts 13. In this embodiment, a transparent substrate 111 coated with a thin transparent conducting layer 112 resides over the array of wicking posts 41, in physical contact with them. Furthermore, the thin transparent conducting layer 112 is connected to load electronics 113 that may include voltage, resistive, and capacitive components. In effect, thin pads 110 and load electronics 113 are chosen to simulate how the human body locally modifies the impedance or capacitance of the display's touchscreen. FIG. 19B illustrates a top view of section 103 on the display which supports the planar allergen filling device. In this case, although filling well 107 has been filled with allergen, allergen 34 has not completely filled wicking post 13.

As an example of the process, FIG. 20A illustrates wicking post 13 filled with allergen extract 35. When the wicking post is filled, fluidic contact is achieved with the conducting sheet 112 modifying the impedance/capacitance at site 114 associated with the respective wicking post coupled by the corresponding small thin pad 110, attached to region 103 of the display. When this occurs, the computing system changes the display color in region 114, as illustrated in FIG. 20B, indicating that the associated wicking post has been filled. Although this example only illustrates the filling of one wicking post, sequential filling of all filling wells and posts may be repeated until the entire planar allergen filling device is loaded with all allergens.

FIG. 21A shows a cross-section view of another embodiment that verifies allergen deposition and transport processes. In this example, conducting lines 120, are placed on the top surface of the top panel 21 (see FIG. 3A). Such lines are made of highly electrically conducting materials; typically, metals. The metals make electrical contact with the wicking post 13. An external circuit 125, probes the electrical conductivity through the wicking post 13. Either electrical resistivity or conductivity may be measured by the external circuit 125.

When filled with allergen, the water-based solutions, result in a significant change of conductivity monitored by external circuit 125 when compared to the unfilled condition. In this manner, the filled status of individual wicking posts may be probed electrically to validate the filling of specific portions of the array. As in the previous embodiment, when this occurs, external circuit 125 interfaced with a computing system would display a region 114 on a display 103 corresponding to its location on the planar allergen filling device. This system and method may eliminate false negative testing errors that are a consequence of incomplete or mis-filling.

Figure 21B:
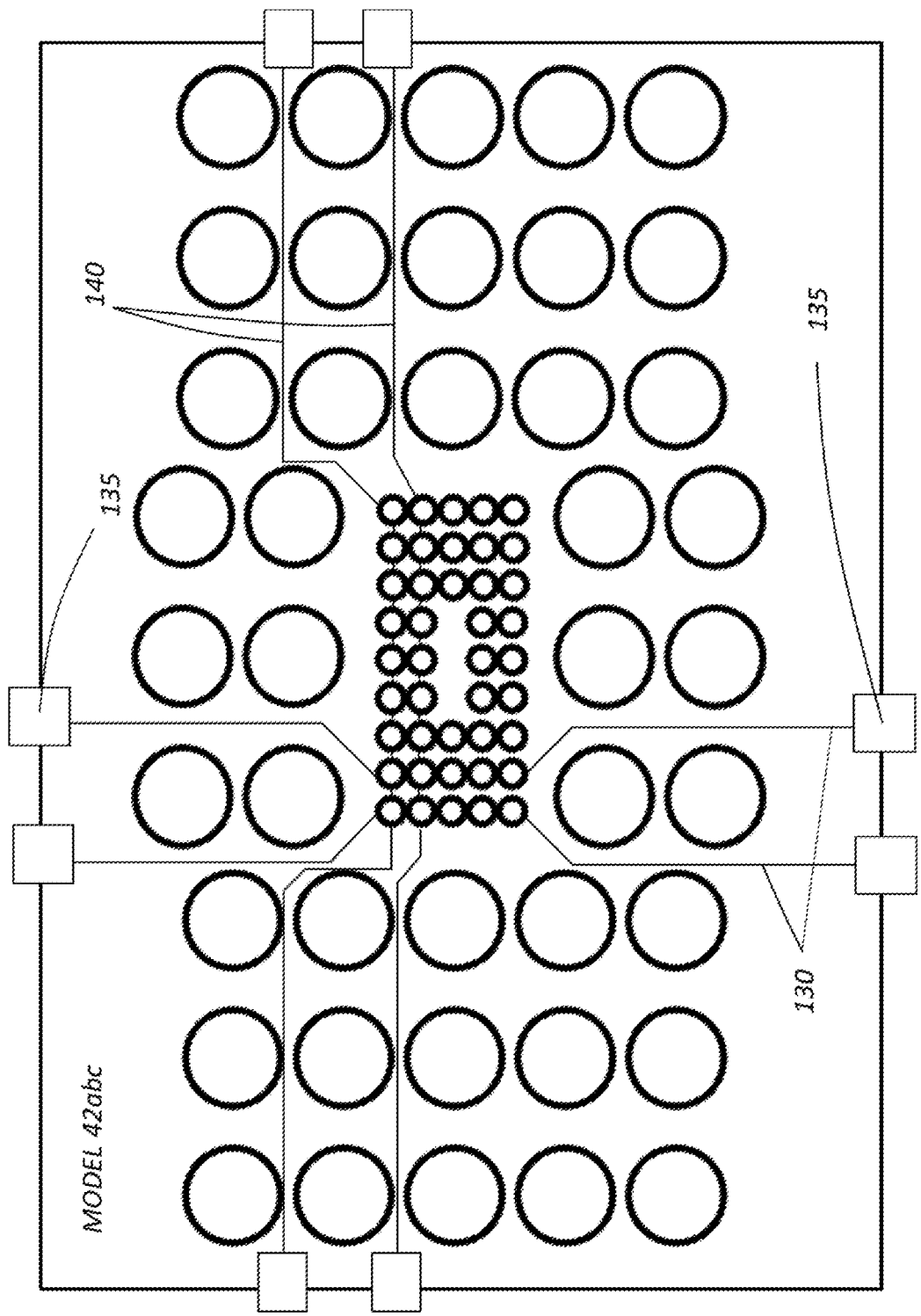

FIG. 21B shows an expanded planar view of a 2D alternative to the allergen filling device 10. Two sets of conducting lines are shown. These conducting lines are further shown in FIG. 21B as vertical 130 and horizontal 140 paths. Also shown are contact pads 135, where connections to the external circuit 125 can be made. Note that only two vertical and two horizontal complete circuits are shown for clarity. In a complete system of this type all the individual wicking posts 13 would be connected to all vertical and horizontal circuits. By electrically scanning such circuits for the change in conductivity indicating the presence of fluid filling, the user can assess the effectiveness of allergen transport and filling of the wicking posts.

Embodiments thus far disclosed that verify effective allergen transport and filling of wicking posts monitor impedance/capacitance (FIG. 20) or resistance/conductivity (FIG. 21). FIG. 22 illustrates yet another embodiment that optically verifies effective allergen extract transport and filling of wicking posts. As stated before, wicking posts can be made of hydrophilic fibers (e.g. cotton), cellulose, foam (e.g. polyurethane), contiguous particulate structures, and similar hydrophilic permeable materials. These materials generally exhibit optical changes when filled with fluids such as allergen extracts. As an example, cotton's refractive index is approximately 1.57, while water's refractive index is approximately 1.33. In this case, when wicking posts having bare cotton on their surfaces are illuminated, multiple optical scattering, absorptive, and refractive events occur resulting in approximately diffuse Lambertian back scattering with low specular reflectance. On the other hand, when wicking posts having bare cotton on their surfaces are filled with allergen extracts (even if colorless) water's refractive index will affect their net reflectivity as it permeates both within and across fibers. The net optical effect is often visible with the naked eye and may be used to identify wicking posts that did not fill (140) from wicking posts that filled (141) as shown in FIG. 22A. This method can be enhanced if digital images are captured of wicking posts before and after filling. When before-after images are digitally subtracted (and possibly enhanced) as shown in FIG. 22B, filled wicking posts 141 will be clearly differentiated from improperly filled posts 140 or unfilled wicking posts. It should be noted that a similar approach may be used to optically verify effective loading of fillable allergen sites 52 and 62 residing on the allergen-loadable microneedle cartridges.

Having thus described several embodiments of the claimed invention, it will be rather apparent to those skilled in the art that the foregoing detailed disclosure is intended to be presented by way of example only and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of the processing elements or sequences, or the use of numbers, letters, or other designations, therefore, is not intended to limit the claimed processes to any order except as may be specified in the claims. Accordingly, the claimed invention is limited only by the following claims and equivalents thereto.

What is claimed is:

1. An allergen-loadable microneedle cartridge comprising:
    at least one substrate;
    a plurality of microneedles protruding from at least one of said substrates, wherein at least one said microneedle is spaced apart from at least one other said microneedle in a microneedle layout;
    a plurality of fillable allergen sites corresponding to said microneedle layout and comprising entrainment structures integrated with at least one of said microneedles, wherein said entrainment structures comprise a patterned hydrophobic layer integrated onto a surface of at least one of said microneedles;
    wherein said plurality of microneedles am configured to penetrate subject skin and deliver allergens from corresponding said entrainment structures.

2. The microneedle cartridge as set forth in claim 1 wherein the entrainment structure comprises formed crevices on the surface of the microneedles.

3. The microneedle cartridge as set forth in claim 1 wherein the entrainment structure comprises an absorbing hydrophilic layer that allows diffusion of the allergen into its volume.

4. An allergen-loadable microneedle cartridge as set forth in claim 1 wherein said cartridge comprises:
    a first said substrate including the plurality of microneedles with at least one said microneedle spaced apart from at least one other said microneedle in a microneedle layout;
    a second said substrate including a plurality of holes and the plurality of fillable allergen sites residing on the plurality of holes corresponding to the microneedle layout on said first substrate;
    at least one compressible element supporting said first and second substrates such that: respective surfaces of said first and second substrates aw parallel; the microneedle layout on the first substrate aligns to the plurality of holes on the second substrate; said plurality of fillable allergen sites on the second substrate facing away from the first substrate.

5. The allergen-loadable microneedle cartridge as set forth in claim 4 wherein said compressible elements are configured to compress as the second substrate contacts the subject's skin upon application of force, allowing the plurality of microneedles on the first substrate to pass through the corresponding plurality of holes and fillable allergen sites on the second substrate, ultimately puncturing the subject's skin.

6. The microneedle cartridge as set forth in claim 5 wherein said compressible elements are configured to decompress upon reduction of force, thereby removing microneedles from the subject's skin after achieving pharmacologically active doses of allergens.

7. The microneedle cartridge as set forth in claim 1, wherein the moat is a rigid three-dimensional (3D) lattice network that does not substantially compress when force is applied during a dosing process.

8. The allergen-loadable microneedle cartridge as set forth in claim 1, wherein said fillable allergen sites comprise absorbing hydrophilic regions.

9. An allergen-loadable microneedle cartridge comprising:
    at least one substrate;
    a plurality of microneedles protruding from at least one of said substrates, wherein at least one said microneedle is spaced apart from at least one other said microneedle in a microneedle layout;
    a plurality of fillable allergen sites corresponding to said microneedle layout and comprising entrainment structures integrated with at least one of said microneedles, wherein the entrainment structure comprises cellulose-based hydrophilic powder adhered to the microneedles;
    wherein said plurality of microneedles are configured to penetrate subject skin and deliver allergens from corresponding said entrainment structures.

10. An allergen-loadable microneedle cartridge comprising:
    a substrate;
    a plurality of discrete fillable allergen sites forming part of a fillable allergen layer that is integrated onto said substrate, wherein said plurality of discrete fillable allergen sites are configured to be loaded with allergens;
    a plurality of hydrophilic moats forming part of the fillable allergen layer and disposed around the fillable allergen sites;
    a plurality of microneedles supported by said substrate, each said microneedle situated within and extending beyond an associated said discrete fillable allergen sites;
    wherein said plurality of discrete fillable allergen sites and associated said plurality of microneedles define allergy test sites configured to test a subject's allergic reactions to allergens loaded into said plurality of discrete fillable allergen sites.

11. The microneedle cartridge as set forth in claim 10, wherein said fillable allergen sites comprise permeable hydrophilic regions.

* * * * *